United States Patent
Yates et al.

(10) Patent No.: US 9,795,436 B2
(45) Date of Patent: Oct. 24, 2017

(54) HARVESTING ENERGY FROM A SURGICAL GENERATOR

(71) Applicant: Ethicon Endo-Surgery, Inc., Cincinnati, OH (US)

(72) Inventors: David C. Yates, West Chester, OH (US); Geoffrey S. Strobl, Williamsburg, OH (US)

(73) Assignee: Ethicon LLC, Guaynabo, PR (US)

( * ) Notice: Subject to any disclaimer, the term of this patent is extended or adjusted under 35 U.S.C. 154(b) by 335 days.

(21) Appl. No.: 14/149,294

(22) Filed: Jan. 7, 2014

(65) Prior Publication Data
US 2015/0190189 A1 Jul. 9, 2015

(51) Int. Cl.
| A61B 18/12 | (2006.01) |
| A61B 18/04 | (2006.01) |
| A61B 17/32 | (2006.01) |
| A61B 18/14 | (2006.01) |
| A61B 17/00 | (2006.01) |

(52) U.S. Cl.
CPC .. *A61B 18/1206* (2013.01); *A61B 17/320068* (2013.01); *A61B 17/320092* (2013.01); *A61B 18/04* (2013.01); *A61B 18/1445* (2013.01); *A61B 2017/00734* (2013.01); *A61B 2018/1226* (2013.01)

(58) Field of Classification Search
CPC ... A61B 2018/1226; A61B 2017/00734; H02J 7/02
See application file for complete search history.

(56) References Cited

U.S. PATENT DOCUMENTS

| 2,366,274 A | 1/1945 | Luth et al. |
| 2,458,152 A | 1/1949 | Eakins |
| 2,510,693 A | 6/1950 | Green |
(Continued)

FOREIGN PATENT DOCUMENTS

| DE | 4300307 A1 | 7/1994 |
| DE | 29623113 U1 | 10/1997 |
(Continued)

OTHER PUBLICATIONS

International Search Report and Written Opinion for International Application No. PCT/US2014/068555 dated Mar. 4, 2015 (12 pages).
(Continued)

*Primary Examiner* — Ronald Hupczey, Jr.

(57) ABSTRACT

Various embodiments are directed surgical devices and systems and methods for use with a surgical device to harvest energy from a surgical generator. The surgical device may comprise an energy storage device. The energy storage device may be in electrical communication with a surgical generator connection to provide energy from a surgical generator to charge the energy storage device and in electrical communication with at least one load component to be powered by the energy storage device. The surgical device may also comprise an end effector at least one energy element for treating tissue. The at least one energy element may be in electrical communication with the surgical generator connection to provide a therapeutic drive signal to the energy element.

13 Claims, 31 Drawing Sheets

(56) References Cited

U.S. PATENT DOCUMENTS

| | | | |
|---|---|---|---|
| 2,867,039 A * | 1/1959 | Zach | B26B 19/28 |
| | | | 30/34.05 |
| 3,166,971 A | 1/1965 | Stoecker | |
| 3,525,912 A * | 8/1970 | Wallin | A47J 43/082 |
| | | | 307/28 |
| 3,580,841 A | 5/1971 | Cadotte et al. | |
| 3,703,651 A | 11/1972 | Blowers | |
| 3,777,760 A | 12/1973 | Essner | |
| 4,005,714 A | 2/1977 | Hiltebrandt | |
| 4,034,762 A | 7/1977 | Cosens et al. | |
| 4,058,126 A | 11/1977 | Leveen | |
| 4,203,430 A | 5/1980 | Takahashi | |
| 4,220,154 A | 9/1980 | Semm | |
| 4,237,441 A | 12/1980 | van Konynenburg et al. | |
| 4,281,785 A | 8/1981 | Brooks | |
| 4,304,987 A | 12/1981 | van Konynenburg | |
| 4,463,759 A | 8/1984 | Garito et al. | |
| 4,492,231 A | 1/1985 | Auth | |
| 4,535,773 A | 8/1985 | Yoon | |
| 4,545,926 A | 10/1985 | Fouts, Jr. et al. | |
| 4,550,870 A | 11/1985 | Krumme et al. | |
| 4,582,236 A | 4/1986 | Hirose | |
| 4,617,927 A | 10/1986 | Manes | |
| 4,735,603 A | 4/1988 | Goodson et al. | |
| 4,761,871 A | 8/1988 | O'Connor et al. | |
| 4,830,462 A | 5/1989 | Karny et al. | |
| 4,849,133 A | 7/1989 | Yoshida et al. | |
| 4,860,745 A | 8/1989 | Farin et al. | |
| 4,878,493 A | 11/1989 | Pasternak et al. | |
| 4,880,015 A | 11/1989 | Nierman | |
| 4,910,389 A | 3/1990 | Sherman et al. | |
| 4,920,978 A | 5/1990 | Colvin | |
| 4,936,842 A | 6/1990 | D'Amelio et al. | |
| 5,020,514 A | 6/1991 | Heckele | |
| 5,061,269 A | 10/1991 | Muller | |
| 5,099,840 A | 3/1992 | Goble et al. | |
| 5,104,025 A | 4/1992 | Main et al. | |
| 5,106,538 A | 4/1992 | Barma et al. | |
| 5,108,383 A | 4/1992 | White | |
| 5,156,633 A | 10/1992 | Smith | |
| 5,160,334 A | 11/1992 | Billings et al. | |
| 5,190,541 A | 3/1993 | Abele et al. | |
| 5,196,007 A | 3/1993 | Ellman et al. | |
| 5,205,459 A | 4/1993 | Brinkerhoff et al. | |
| 5,217,460 A | 6/1993 | Knoepfler | |
| 5,234,428 A | 8/1993 | Kaufman | |
| 5,258,006 A | 11/1993 | Rydell et al. | |
| 5,285,945 A | 2/1994 | Brinkerhoff et al. | |
| 5,290,286 A | 3/1994 | Parins | |
| 5,309,927 A | 5/1994 | Welch | |
| 5,318,564 A | 6/1994 | Eggers | |
| 5,318,589 A | 6/1994 | Lichtman | |
| 5,330,471 A | 7/1994 | Eggers | |
| 5,330,502 A | 7/1994 | Hassler et al. | |
| 5,339,723 A | 8/1994 | Huitema | |
| 5,342,359 A | 8/1994 | Rydell | |
| 5,361,583 A | 11/1994 | Huitema | |
| 5,383,874 A | 1/1995 | Jackson et al. | |
| 5,387,207 A | 2/1995 | Dyer et al. | |
| 5,389,098 A | 2/1995 | Tsuruta et al. | |
| 5,395,312 A | 3/1995 | Desai | |
| 5,395,363 A | 3/1995 | Billings et al. | |
| 5,395,364 A | 3/1995 | Anderhub et al. | |
| 5,396,900 A | 3/1995 | Slater et al. | |
| 5,403,312 A | 4/1995 | Yates et al. | |
| 5,417,709 A | 5/1995 | Slater | |
| 5,428,504 A | 6/1995 | Bhatla | |
| 5,429,131 A | 7/1995 | Scheinman et al. | |
| 5,443,463 A | 8/1995 | Stern et al. | |
| 5,445,638 A | 8/1995 | Rydell et al. | |
| 5,451,227 A | 9/1995 | Michaelson | |
| 5,458,598 A | 10/1995 | Feinberg et al. | |
| 5,465,895 A | 11/1995 | Knodel et al. | |
| 5,472,443 A | 12/1995 | Cordis et al. | |
| 5,476,479 A | 12/1995 | Green et al. | |
| 5,480,409 A | 1/1996 | Riza | |
| 5,484,436 A | 1/1996 | Eggers et al. | |
| 5,486,189 A | 1/1996 | Mudry et al. | |
| 5,496,317 A | 3/1996 | Goble et al. | |
| 5,504,650 A | 4/1996 | Katsui et al. | |
| 5,509,922 A | 4/1996 | Aranyi et al. | |
| 5,511,556 A | 4/1996 | DeSantis | |
| 5,520,704 A | 5/1996 | Castro et al. | |
| 5,522,839 A | 6/1996 | Pilling | |
| 5,531,744 A | 7/1996 | Nardella et al. | |
| 5,542,916 A | 8/1996 | Hirsch et al. | |
| 5,558,671 A | 9/1996 | Yates | |
| 5,563,179 A | 10/1996 | Stone et al. | |
| 5,571,121 A | 11/1996 | Heifetz | |
| 5,573,534 A | 11/1996 | Stone | |
| 5,584,830 A | 12/1996 | Ladd et al. | |
| 5,599,350 A | 2/1997 | Schulze et al. | |
| 5,607,450 A | 3/1997 | Zvenyatsky et al. | |
| 5,611,813 A | 3/1997 | Lichtman | |
| 5,618,307 A | 4/1997 | Donlon et al. | |
| 5,624,452 A | 4/1997 | Yates | |
| 5,632,432 A | 5/1997 | Schulze et al. | |
| 5,647,871 A | 7/1997 | Levine et al. | |
| 5,658,281 A | 8/1997 | Heard | |
| 5,662,667 A | 9/1997 | Knodel | |
| 5,665,085 A | 9/1997 | Nardella | |
| 5,665,100 A | 9/1997 | Yoon | |
| 5,674,219 A | 10/1997 | Monson et al. | |
| 5,674,220 A | 10/1997 | Fox et al. | |
| 5,688,270 A | 11/1997 | Yates et al. | |
| 5,693,051 A | 12/1997 | Schulze et al. | |
| 5,709,680 A | 1/1998 | Yates et al. | |
| 5,713,896 A | 2/1998 | Nardella | |
| 5,716,366 A | 2/1998 | Yates | |
| 5,723,970 A * | 3/1998 | Bell | H02J 7/045 |
| | | | 320/140 |
| 5,735,848 A | 4/1998 | Yates et al. | |
| 5,743,906 A | 4/1998 | Parins et al. | |
| 5,752,973 A | 5/1998 | Kieturakis | |
| 5,755,717 A | 5/1998 | Yates et al. | |
| 5,762,255 A | 6/1998 | Chrisman et al. | |
| 5,779,701 A | 7/1998 | McBrayer et al. | |
| 5,782,834 A | 7/1998 | Lucey et al. | |
| 5,792,135 A | 8/1998 | Madhani et al. | |
| 5,792,138 A | 8/1998 | Shipp | |
| 5,796,188 A * | 8/1998 | Bays | A61B 17/1628 |
| | | | 310/40 MM |
| 5,797,941 A | 8/1998 | Schulze et al. | |
| 5,800,432 A | 9/1998 | Swanson | |
| 5,800,449 A | 9/1998 | Wales | |
| 5,807,393 A | 9/1998 | Williamson, IV et al. | |
| 5,810,811 A | 9/1998 | Yates et al. | |
| 5,817,033 A | 10/1998 | DeSantis et al. | |
| 5,817,084 A | 10/1998 | Jensen | |
| 5,817,093 A | 10/1998 | Williamson, IV et al. | |
| 5,836,909 A | 11/1998 | Cosmescu | |
| 5,836,943 A | 11/1998 | Miller, III | |
| 5,853,412 A | 12/1998 | Mayenberger | |
| 5,876,401 A | 3/1999 | Schulze et al. | |
| 5,878,193 A | 3/1999 | Wang et al. | |
| 5,880,668 A | 3/1999 | Hall | |
| 5,891,142 A | 4/1999 | Eggers et al. | |
| 5,906,625 A | 5/1999 | Bito et al. | |
| 5,921,956 A | 7/1999 | Grinberg et al. | |
| 5,984,938 A | 11/1999 | Yoon | |
| 6,003,517 A | 12/1999 | Sheffield et al. | |
| 6,013,052 A | 1/2000 | Durman et al. | |
| 6,024,741 A | 2/2000 | Williamson, IV et al. | |
| 6,024,744 A | 2/2000 | Kese et al. | |
| 6,033,399 A | 3/2000 | Gines | |
| 6,039,734 A | 3/2000 | Goble | |
| 6,050,996 A | 4/2000 | Schmaltz et al. | |
| 6,063,098 A | 5/2000 | Houser et al. | |
| 6,068,629 A | 5/2000 | Haissaguerre et al. | |
| 6,074,389 A | 6/2000 | Levine et al. | |
| 6,091,995 A | 7/2000 | Ingle et al. | |
| 6,099,483 A | 8/2000 | Palmer et al. | |
| 6,099,550 A | 8/2000 | Yoon | |
| H1904 H | 10/2000 | Yates et al. | |

(56) References Cited

U.S. PATENT DOCUMENTS

| | | |
|---|---|---|
| 6,132,368 A | 10/2000 | Cooper |
| 6,144,402 A | 11/2000 | Norsworthy et al. |
| 6,152,923 A | 11/2000 | Ryan |
| 6,162,208 A | 12/2000 | Hipps |
| 6,174,309 B1 | 1/2001 | Wrublewski et al. |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,702 B2 | 10/2002 | Schulze et al. |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |

(56) References Cited

U.S. PATENT DOCUMENTS

| | | |
|---|---|---|
| 7,597,693 B2 | 10/2009 | Garrison |
| 7,604,150 B2 | 10/2009 | Boudreaux |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,722,527 B2 | 5/2010 | Bouchier et al. |
| 7,722,607 B2 | 5/2010 | Dumbauld et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,789,883 B2 | 9/2010 | Takashino et al. |
| 7,803,156 B2 | 9/2010 | Eder et al. |
| 7,806,891 B2 | 10/2010 | Nowlin et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,846,159 B2 | 12/2010 | Morrison et al. |
| 7,846,160 B2 | 12/2010 | Payne et al. |
| 7,879,035 B2 | 2/2011 | Garrison et al. |
| 7,879,070 B2 | 2/2011 | Ortiz et al. |
| 7,896,875 B2 * | 3/2011 | Heim .............. A61B 18/1402 606/39 |
| 7,901,400 B2 | 3/2011 | Wham et al. |
| 7,909,220 B2 | 3/2011 | Viola |
| 7,919,184 B2 | 4/2011 | Mohapatra et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,056,720 B2 | 11/2011 | Hawkes |
| 8,058,771 B2 | 11/2011 | Giordano et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,221,415 B2 | 7/2012 | Francischelli |
| 8,241,235 B2 * | 8/2012 | Kahler ............. A61B 17/1628 602/32 |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,357,158 B2 | 1/2013 | McKenna et al. |
| 8,377,059 B2 | 2/2013 | Deville et al. |
| 8,397,971 B2 | 3/2013 | Yates et al. |
| 8,414,577 B2 | 4/2013 | Boudreaux et al. |
| 8,430,876 B2 | 4/2013 | Kappus et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,486,057 B2 | 7/2013 | Behnke, II |
| 8,496,682 B2 | 7/2013 | Guerra et al. |
| 8,535,311 B2 | 9/2013 | Schall |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| 8,613,383 B2 | 12/2013 | Beckman et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,647,350 B2 | 2/2014 | Mohan et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,044,243 B2 | 6/2015 | Johnson et al. |
| 9,044,256 B2 | 6/2015 | Cadeddu et al. |
| 9,060,770 B2 | 6/2015 | Shelton, IV et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,149,324 B2 | 10/2015 | Huang et al. |
| 9,179,912 B2 | 11/2015 | Yates et al. |
| 9,192,431 B2 | 11/2015 | Woodruff et al. |

(56) References Cited

U.S. PATENT DOCUMENTS

| | | |
|---|---|---|
| 9,204,879 B2 | 12/2015 | Shelton, IV |
| 9,226,751 B2 | 1/2016 | Shelton, IV et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,283,027 B2 | 3/2016 | Monson et al. |
| 9,295,514 B2 | 3/2016 | Shelton, IV et al. |
| 9,314,292 B2 | 4/2016 | Trees et al. |
| 2002/0022836 A1 | 2/2002 | Goble et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0241589 A1* | 10/2006 | Heim ............... A61B 18/1402 606/48 |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087212 A1 | 4/2011 | Aldridge et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0125177 A1* | 5/2011 | Yates ............... A61B 17/07207 606/170 |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Horner |
| 2011/0306967 A1 | 12/2011 | Payne et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116265 A1* | 5/2012 | Houser ............ A61B 17/00234 601/2 |
| 2012/0116379 A1 | 5/2012 | Yates et al. |
| 2012/0116380 A1* | 5/2012 | Madan ............. A61B 17/00234 606/33 |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2013/0023925 A1 | 1/2013 | Mueller |

(56) References Cited

U.S. PATENT DOCUMENTS

| | | |
|---|---|---|
| 2013/0030433 A1 | 1/2013 | Heard |
| 2013/0079762 A1 | 3/2013 | Twomey et al. |
| 2013/0085496 A1 | 4/2013 | Unger et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0131660 A1 | 5/2013 | Monson et al. |
| 2013/0253256 A1 | 9/2013 | Griffith et al. |
| 2013/0253502 A1 | 9/2013 | Aronow et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0148806 A1 | 5/2014 | Witt et al. |
| 2014/0194914 A1 | 7/2014 | Hunt et al. |
| 2014/0194915 A1 | 7/2014 | Johnson et al. |
| 2014/0257284 A1 | 9/2014 | Artale |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0196352 A1 | 7/2015 | Beckman et al. |
| 2015/0201953 A1 | 7/2015 | Strobl et al. |
| 2015/0230853 A1 | 8/2015 | Johnson et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |

FOREIGN PATENT DOCUMENTS

| | | |
|---|---|---|
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| EP | 2578172 A2 | 4/2013 |
| EP | 2508143 B1 | 2/2014 |
| GB | 2472216 A | 2/2011 |
| JP | H 08-229050 | 9/1996 |
| JP | 2008-018226 | 1/2008 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/078051 A2 | 9/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/154157 A1 | 10/2013 |
| WO | WO 2015/197395 A8 | 12/2015 |

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hormann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

(56) References Cited

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the Asme, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979). (book—not attached).

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, [Value Analysis Brief], LigaSure Advance™ Pistol Grip, dated Rev. Apr. 2010 (7 pages).

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

Covidien Brochure, The LigaSure Precise™ Instrument, dated Mar. 2011 (2 pages).

Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S D027541.

Jang, J. et al. "Neuro-fuzzy and Soft Computing." Prentice Hall, 1997, pp. 13-89, 199-293, 335-393,453-496, 535-549.

Douglas, S.C. "Introduction to Adaptive Filter". Digital Signal Processing Handbook. Ed. Vijay K. Madisetti and Douglas B. Williams. Boca Raton: CRC Press LLC, 1999.

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

International Preliminary Report on Patentability for PCT/US2014/068555 dated Jul. 12, 2016 (8 pages).

\* cited by examiner

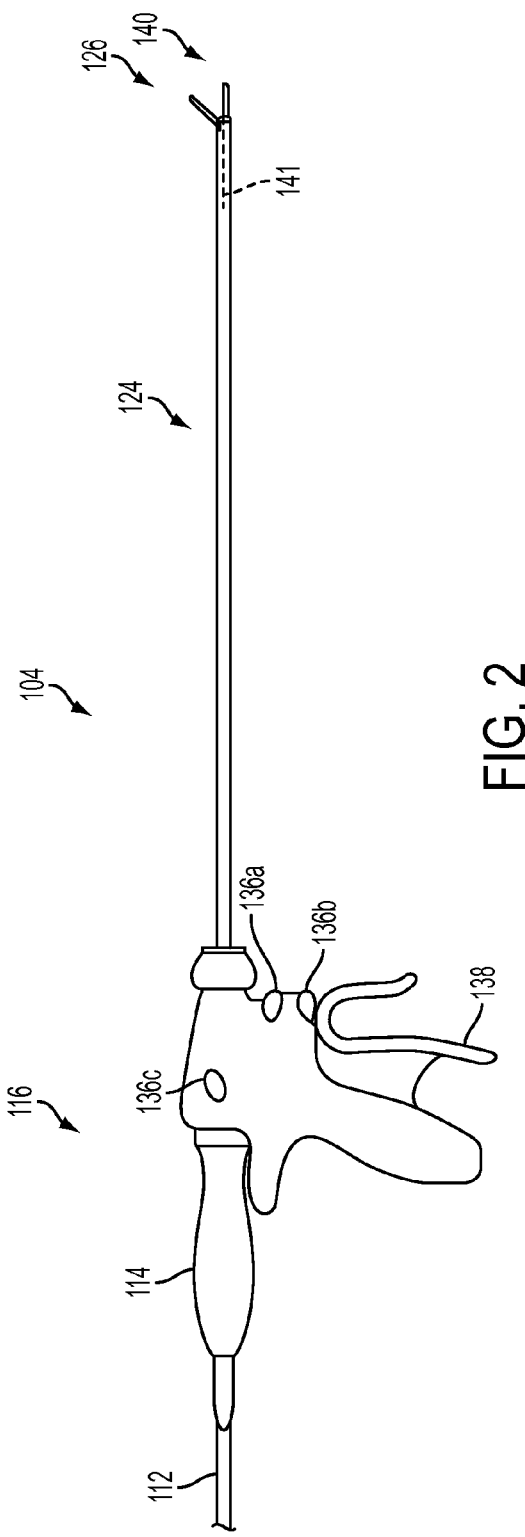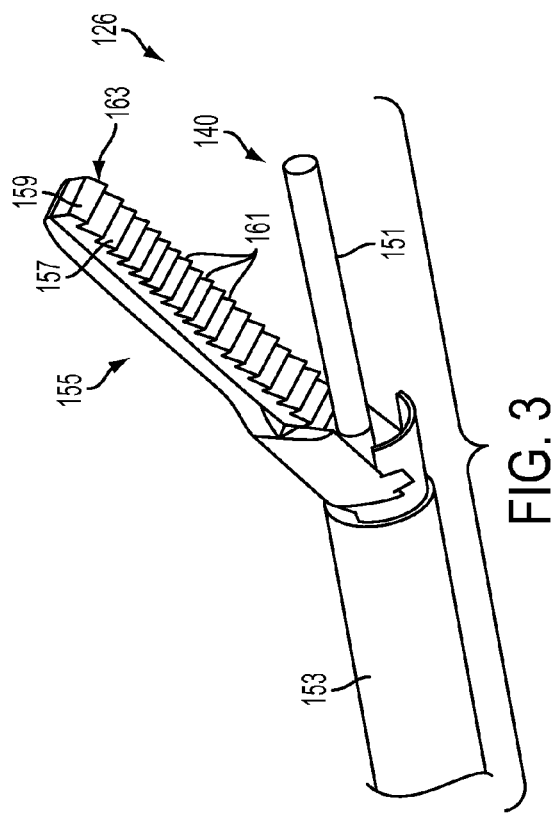

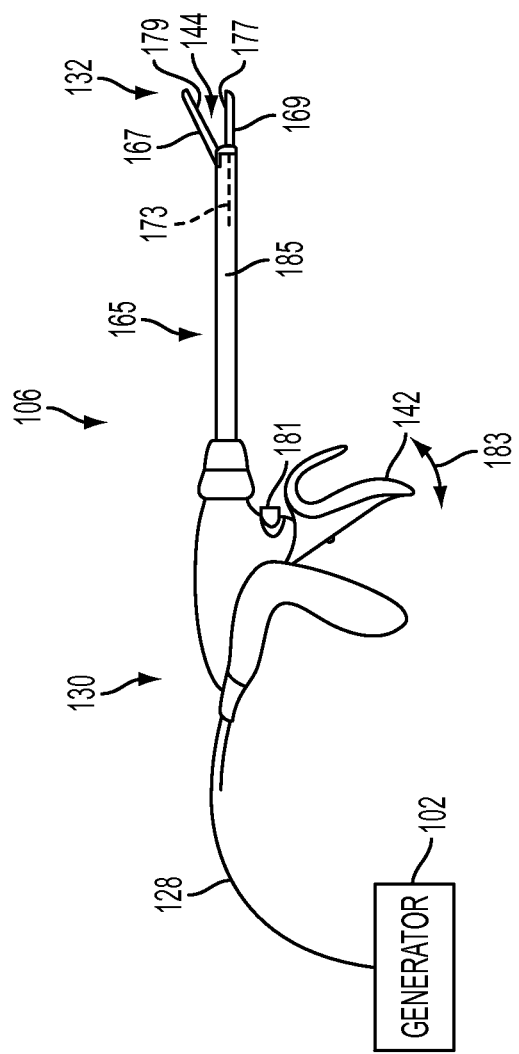

HARVESTING ENERGY FROM A SURGICAL GENERATOR

BACKGROUND

Various embodiments are directed to surgical devices and/or associated surgical generators for harvesting energy provided by the generator and storing the harvested energy at the surgical device for use in powering functionality of the surgical device.

Electrosurgical devices for applying electrical energy to tissue in order to treat and/or destroy the tissue are commonly used in surgical procedures. An electrosurgical device may comprise a hand piece and an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue may form hemostatic seals within the tissue and/or between tissues and thus may be particularly useful for sealing blood vessels, for example. The end effector of an electrosurgical device may also comprise a cutting member that is movable relative to the tissue and the electrodes to transect the tissue.

Electrical energy applied by an electrosurgical device can be transmitted to the instrument by a generator in communication with the hand piece. The electrical energy may be in the form of radio frequency ("RF") energy. RF energy is a form of electrical energy that may be in the frequency range of 300 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

Ultrasonic surgical devices, such as ultrasonic scalpels, are another type of powered surgical devices used in surgical procedures. Depending upon specific device configurations and operational parameters, ultrasonic surgical devices can provide substantially simultaneous transection of tissue and homeostasis by coagulation, desirably minimizing patient trauma. An ultrasonic surgical device may comprise a hand piece containing an ultrasonic transducer, and an instrument coupled to the ultrasonic transducer having a distally-mounted end effector (e.g., a blade tip) to cut and seal tissue. In some cases, the instrument may be permanently affixed to the hand piece. In other cases, the instrument may be detachable from the hand piece, as in the case of a disposable instrument or an instrument that is interchangeable between different hand pieces. The end effector transmits ultrasonic energy to tissue brought into contact with the end effector to realize cutting and sealing action. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures and can be transmitted to the end effector by an ultrasonic generator in communication with the hand piece. Vibrating at high frequencies (e.g., 55,500 times per second), the ultrasonic blade denatures protein in the tissue to form a sticky coagulum. Pressure exerted on tissue by the blade surface collapses blood vessels and allows the coagulum to form a hemostatic seal. A clinician can control the cutting speed and coagulation by the force applied to the tissue by the end effector, the time over which the force is applied and the selected excursion level of the end effector.

Electrosurgical and ultrasonic devices that operate in conjunction with an external generator typically do not carry an on-board power supply. This limits the functionality that can be provided by the devices themselves. For example, in generator-connected surgical devices it is not currently feasible to include components that consume high levels of power such as, for example, motors, powered sensors, microprocessors, etc.

SUMMARY

Various embodiments are directed surgical devices and systems and methods for use with a surgical device to harvest energy from a surgical generator. The surgical device may comprise an energy storage device. The energy storage device may be in electrical communication with a surgical generator connection to provide energy from a surgical generator to charge the energy storage device and in electrical communication with at least one load component to be powered by the energy storage device. The surgical device may also comprise an end effector and at least one energy element for treating tissue. The at least one energy element may be in electrical communication with the surgical generator connection to provide a therapeutic drive signal to the energy element.

FIGURES

The novel features of the various embodiments are set forth with particularity in the appended claims. The described embodiments, however, both as to organization and methods of operation, may be best understood by reference to the following description, taken in conjunction with the accompanying drawings in which:

FIG. 2 illustrates one embodiment of an example ultrasonic device that may be used for transection and/or sealing.

FIG. 3 illustrates one embodiment of the end effector of the example ultrasonic device of FIG. 2.

FIG. 4 illustrates one embodiment of an example electrosurgical device that may also be used for transection and sealing.

DESCRIPTION

Figure 1:
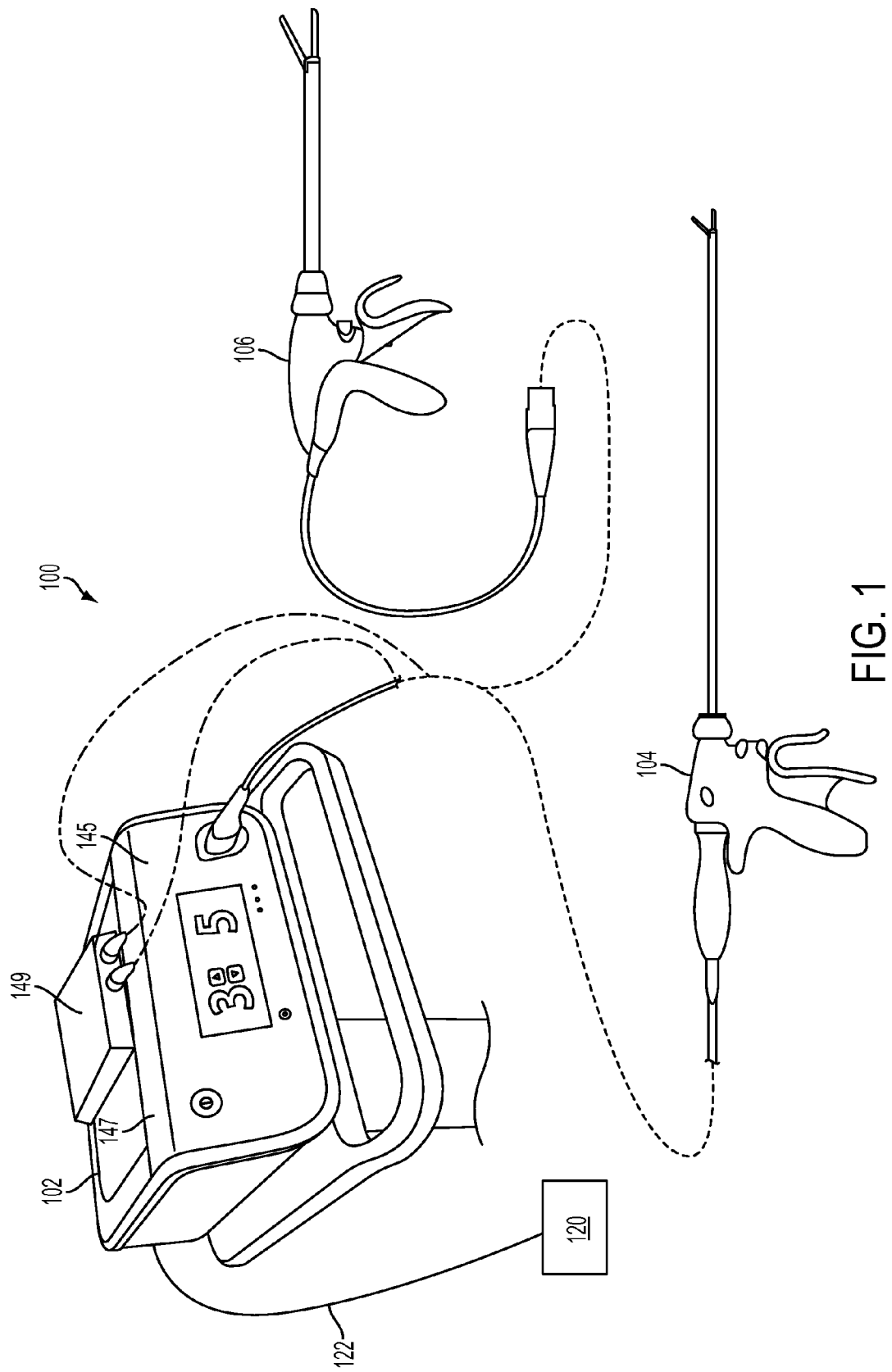
FIG. 1 illustrates one embodiment of a surgical system comprising a generator and various surgical devices usable therewith.

Before explaining various embodiments of surgical devices and generators in detail, it should be noted that the illustrative embodiments are not limited in application or use to the details of construction and arrangement of parts illustrated in the accompanying drawings and description. The illustrative embodiments may be implemented or incorporated in other embodiments, variations and modifications, and may be practiced or carried out in various ways. Further, unless otherwise indicated, the terms and expressions employed herein have been chosen for the purpose of describing the illustrative embodiments for the convenience of the reader and are not for the purpose of limitation thereof. Also, it will be appreciated that one or more of the following-described embodiments, expressions of embodiments and/or examples, can be combined with any one or more of the other following-described embodiments, expressions of embodiments and/or examples.

Various embodiments are directed to surgical devices and/or associated surgical generators for harvesting energy provided by the generator and storing the harvested energy at the surgical device for use in powering functionality of the surgical device. In various embodiments, a surgical device may comprise an energy storage device, an end effector and at least one energy element for treating tissue. For example, when the surgical device is an electrosurgical device, the at least one energy element may comprise one or more electrodes positioned in the end effector. Also, for example, when the surgical device is an ultrasonic device, the at least one energy element may comprise a transducer mechanically coupled to an ultrasonic blade (e.g., via an intermediate wave guide).

The energy storage device may be in electrical communication with a surgical generator connection. The surgical generator connection may, in turn, be in communication with a surgical generator. In some embodiments, the surgical device also comprises a switch positioned to alternately to connect the surgical generator connection to the energy storage device or to the at least one energy element. For example, the surgical generator may alternately provide a charge signal or a therapeutic drive signal. When the surgical generator provides the charge signal, the surgical device may configure the switch so that the charge signal is provided to the energy storage device, thus charging the energy storage device. When the generator provides the therapeutic drive signal, the surgical device may configure the switch so that the therapeutic drive signal is provided to the at least one energy element. In some embodiments, the generator may provide a combined signal comprising a charge signal component and a therapeutic drive signal component. The surgical device may comprise a signal separator circuit positioned to receive the combined signal and divide it into a charge signal portion, provided to the energy storage device, and a therapeutic drive signal portion, provided to the at least one energy element. The energy storage device and associated circuitry may physically positioned at any suitable location. For example, the energy storage device may be positioned in an enclosure separate from the generator and the surgical device (e.g. a break-out box). Also, in some embodiments, the energy storage device and associated circuitry may be integral to the generator itself and/or integral to the surgical device.

Once charged, the energy storage device may be utilized to power various load components present at the surgical device. Load components may comprise any component of the surgical device for which electrical power is required and/or desirable. Examples of load devices include, for example, sensors for sensing a property of the surgical device and/or tissue being acted upon by the surgical device. Load components may also include a display or displays for providing a clinician with various information regarding the surgical device, the patient, conditions or properties of the tissue, the generator, etc. In some embodiments, the load components may comprise a transmission circuit for communicating to other devices the information about the surgical device, the patient, conditions or properties of the tissue, the generator, etc. Also, in some embodiments, the load components may comprise a motor or drive train. The motor and/or drive train may be mechanically coupled to, for example, cause or assist firing of the surgical device, articulate the surgical device, etc. These and other benefits of embodiments of the present invention will be apparent from the description to follow.

It will be appreciated that the terms "proximal" and "distal" are used herein with reference to a clinician gripping a hand piece. Thus, an end effector is distal with respect to the more proximal hand piece. It will be further appreciated that, for convenience and clarity, spatial terms such as "top" and "bottom" may also be used herein with respect to the clinician gripping the hand piece. However, surgical devices are used in many orientations and positions, and these terms are not intended to be limiting and absolute.

FIG. 1 illustrates one embodiment of a surgical system 100 comprising a generator 102 configurable for use with surgical devices. According to various embodiments, the generator 102 may be configurable for use with surgical devices of different types, including, for example, the ultrasonic surgical device 104 and electrosurgical or RF surgical device 106. Although in the embodiment of FIG. 1 the generator 102 is shown separate from the surgical devices 104, 106, in certain embodiments the generator 102 may be formed integrally with either of the surgical devices 104, 106 to form a unitary surgical system. A break-out box 149 is shown placed on top of the generator 102. The break-out box may house circuitry or other hardware that is not included in the generator 102 or the devices 104, 106 themselves. For example, the break-out box 149 may house the energy harvesting circuit 1302 (e.g., FIG. 13) in embodiments where that circuit is not integral to either the generator 102 or the device 104, 106. For example, the break-out box 149 may be electrically coupled to the generator (e.g., surgical generator connection 1350 of FIG. 13) and to the device (e.g., connections 1352 and 1352 of FIG. 13).

FIG. 2 illustrates one embodiment of an example ultrasonic device 104 that may be used for transection and/or sealing. The device 104 may comprise a hand piece 116 which may, in turn, comprise an ultrasonic transducer 114. The transducer 114 may be in electrical communication with the generator 102, for example, via a cable 112 (e.g., a multi-conductor cable). The transducer 114 may comprise piezoceramic elements, or other elements or components suitable for converting the electrical energy of a drive signal into mechanical vibrations. When activated by the generator 102, the ultrasonic transducer 114 may cause longitudinal vibration. The vibration may be transmitted through an instrument portion 124 of the device 104 (e.g., via a waveguide embedded in an outer sheath) to an end effector 126 of the instrument portion 124.

FIG. 3 illustrates one embodiment of the end effector 126 of the example ultrasonic device 104. The end effector 126 may comprise a blade 151 that may be coupled to the ultrasonic transducer 114 via the wave guide (not shown). When driven by the transducer 114, the blade 151 may vibrate and, when brought into contact with tissue, may cut and/or coagulate the tissue, as described herein. According to various embodiments, and as illustrated in FIG. 3, the end effector 126 may also comprise a clamp arm 155 that may be configured for cooperative action with the blade 151 of the end effector 126. With the blade 151, the clamp arm 155 may comprise a set of jaws 140. The clamp arm 155 may be pivotally connected at a distal end of a shaft 153 of the instrument portion 124. The clamp arm 155 may include a clamp arm tissue pad 163, which may be formed from TEFLON® or other suitable low-friction material. The pad 163 may be mounted for cooperation with the blade 151, with pivotal movement of the clamp arm 155 positioning the clamp pad 163 in substantially parallel relationship to, and in contact with, the blade 151. By this construction, a tissue bite to be clamped may be grasped between the tissue pad 163 and the blade 151. The tissue pad 163 may be provided with a sawtooth-like configuration including a plurality of axially spaced, proximally extending gripping teeth 161 to enhance the gripping of tissue in cooperation with the blade 151. The clamp arm 155 may transition from the open position shown in FIG. 3 to a closed position (with the clamp arm 155 in contact with or proximity to the blade 151) in any suitable manner. For example, the hand piece 116 may comprise a jaw closure trigger 138. When actuated by a clinician, the jaw closure trigger 138 may pivot the clamp arm 155 in any suitable manner. For example, the jaw closure trigger 138 may be coupled to a jaw closure member 141 extending through the shaft 124 to the clamp arm 155. Proximal motion of the jaw closure trigger 138 may cause corresponding proximal motion of the jaw closure member 141, which may pull the clamp arm 155 towards the blade.

Figure 8:
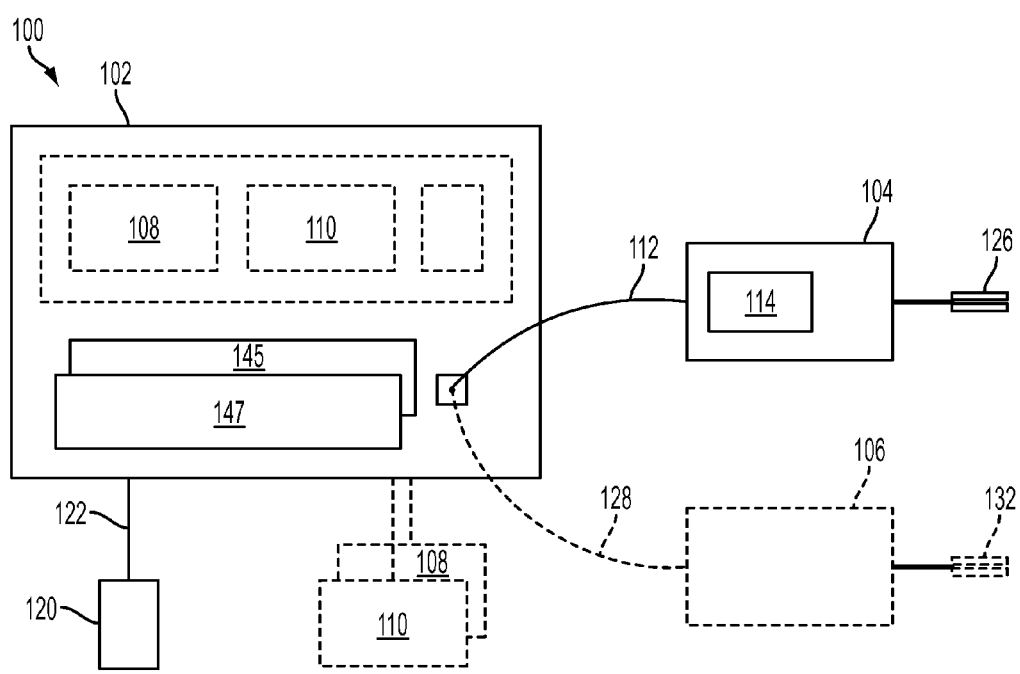
FIG. 8 illustrates one embodiment of the surgical system of FIG. 1.

The generator 102 may be activated to provide the drive signal to the transducer 114 in any suitable manner. For example, the generator 102 may comprise a foot switch 120 coupled to the generator 102 via a footswitch cable 122 (FIGS. 1, 8). A clinician may activate the transducer 114, and thereby the blade 151, by depressing the foot switch 120. In addition, or instead of the foot switch 120 some embodiments of the device 104 may utilize one or more switches or buttons positioned on the hand piece 116 that, when activated, may cause the generator 102 to activate the transducer 114. In some embodiments, the hand piece 116 may comprise a pair of buttons 136a, 136b positioned relative to the closure trigger 138 to allow the clinician to operate the buttons 136a, 136b with an index finger, for example, while gripping the closure trigger 138. In other embodiments, the buttons 136a, 136b may be replaced with a single similarly located button. Also, for example, one or more additional buttons, such as 136c, may be positioned on an upper portion of the hand piece 116. For example, the button 136c may be configured to, when depressed, cause the generator 102 to provide a pulsed output. The pulses may be provided at any suitable frequency and grouping, for example. In certain embodiments, the power level of the pulses may be the power levels set utilizing buttons 136a, 136b, as described above. Also, in some embodiments, the generator 102 may be activated based on the position of the jaw closure trigger 138, (e.g., as the clinician depresses the jaw closure trigger 138 to close the jaws 140, ultrasonic energy may be applied).

The various buttons 136a, 136b, 136c may be hardwired and/or programmable to, when depressed, bring about various effects on the drive signal provided to the transducer 114. For example, in some embodiments, the state of the buttons 136a, 136b be communicated to the generator 102. In response to the state of the buttons, the generator 102 may determine an operating mode of the device 104, expressed as the form of the drive signal provided by the generator 102. When the button 136a is depressed, for example, the ultrasonic generator 102 may provide a maximum drive signal to the transducer 114, causing it to produce maximum ultrasonic energy output. Depressing button 136b may cause the generator 102 to provide a user-selectable drive signal to the transducer 114, causing it to produce less than the maximum ultrasonic energy output.

It will be appreciated that the ultrasonic device 104 may comprise any combination of the buttons 136a, 136b, 136c. For example, the device 104 could be configured to have only two buttons: a button 136a for producing maximum ultrasonic energy output and a button 136c for producing a pulsed output at either the maximum or less than maximum power level per. In this way, the drive signal output configuration of the generator 102 could be 5 continuous signals and 5 or 4 or 3 or 2 or 1 pulsed signals. In certain embodiments, the specific drive signal configuration may be controlled based upon, for example, EEPROM settings in the generator 102 and/or user power level selection(s).

In certain embodiments, a two-position switch may be provided as an alternative to a button 136c. For example, a device 104 may include a button 136a for producing a continuous output at a maximum power level and a two-position button 136b. In a first detented position, button 136b may produce a continuous output at a less than maximum power level, and in a second detented position the button 136b may produce a pulsed output (e.g., at either a maximum or less than maximum power level, depending upon the EEPROM settings).

In some embodiments, the end effector 126 may also comprise a pair of electrodes 159, 157. The electrodes 159, 157 may be in communication with the generator 102, for example, via the cable 128. The electrodes 159, 157 may be used, for example, to measure an impedance of a tissue bite present between the clamp arm 155 and the blade 151. The generator 102 may provide a signal (e.g., a non-therapeutic signal) to the electrodes 159, 157. The impedance of the tissue bite may be found, for example, by monitoring the current, voltage, etc. of the signal. In some embodiments, the non-therapeutic signal provided to the electrodes 159, 157 may be provided by the surgical device 106 itself. For example, the electrodes 159, 157 may be load components powered by the energy storage device described herein.

FIG. 4 illustrates one embodiment of an example electrosurgical device 106 that may also be used for transection and sealing. According to various embodiments, the transection and sealing device 106 may comprise a hand piece assembly 130, a shaft 165 and an end effector 132. The shaft 165 may be rigid, as shown, (e.g., for laparoscopic and/or open surgical application) or flexible, (e.g., for endoscopic application). In various embodiments, the shaft 165 may comprise one or more articulation points. The end effector 132 may comprise jaws 144 having a first jaw member 167 and a second jaw member 169. A translating member 173 may extend within the shaft 165 from the end effector 132 to the hand piece 130. At the hand piece 130, the shaft 165 may be directly or indirectly coupled to a jaw closure trigger 142 (FIG. 4).

The jaw members 167, 169 of the end effector 132 may comprise respective electrodes 177, 179. The electrodes 177, 179 may be connected to the generator 102 via electrical leads 187a, 187b (FIG. 5) extending from the end effector 132 through the shaft 165 and hand piece 130 and ultimately to the generator 102 (e.g., by a multi-conductor cable 128). The generator 102 may provide a drive signal to the electrodes 177, 179 to bring about a therapeutic effect to tissue present within the jaw members 167, 169. The electrodes 177, 179 may comprise an active electrode and a return electrode, wherein the active electrode and the return electrode can be positioned against, or adjacent to, the tissue to be treated such that current can flow from the active electrode to the return electrode through the tissue. As illustrated in FIG. 4, the end effector 132 is shown with the jaw members 167, 169 in an open position.

Figure 5:
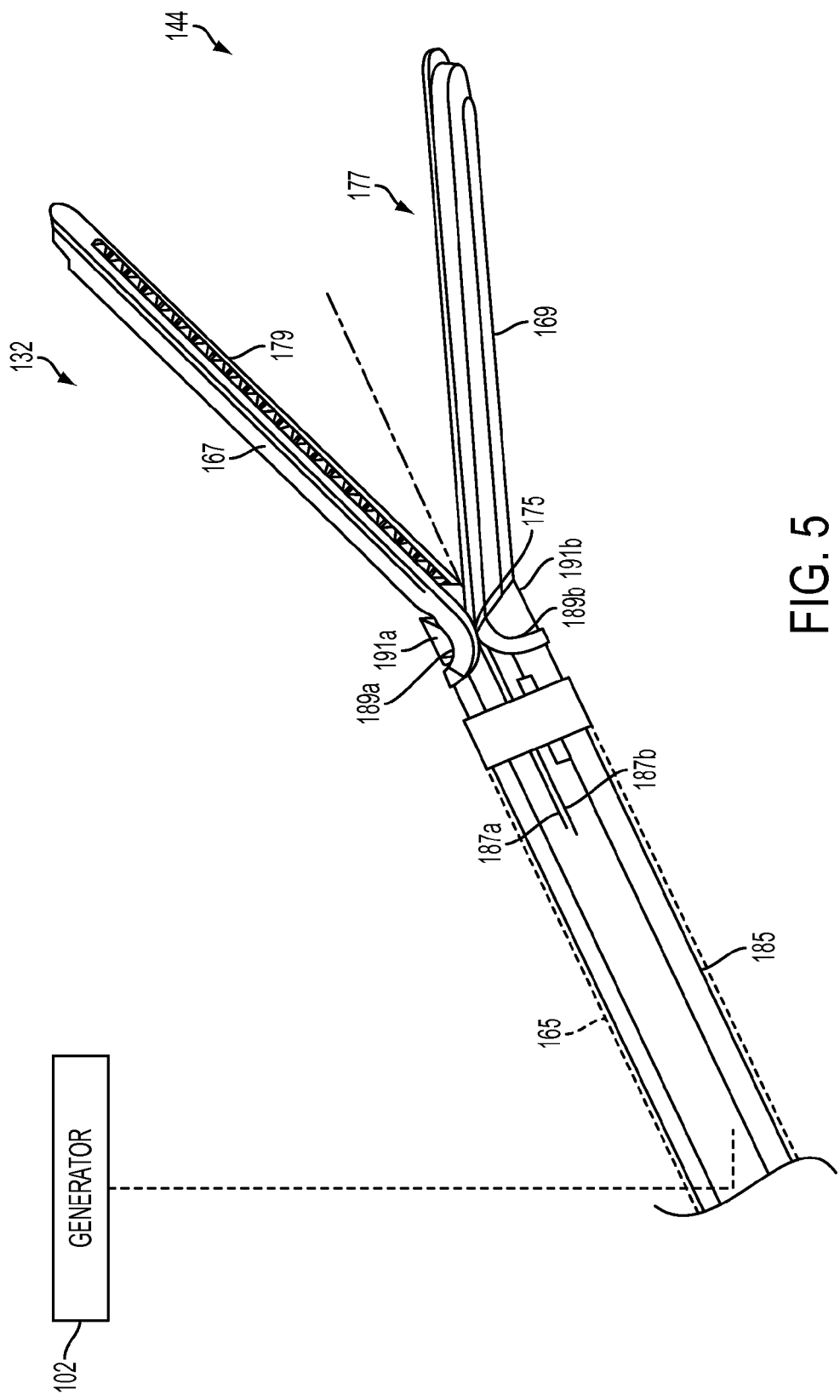
FIGS. 5, 6 and 7 illustrate one embodiment of the end effector shown in FIG. 4.
Figure 6:
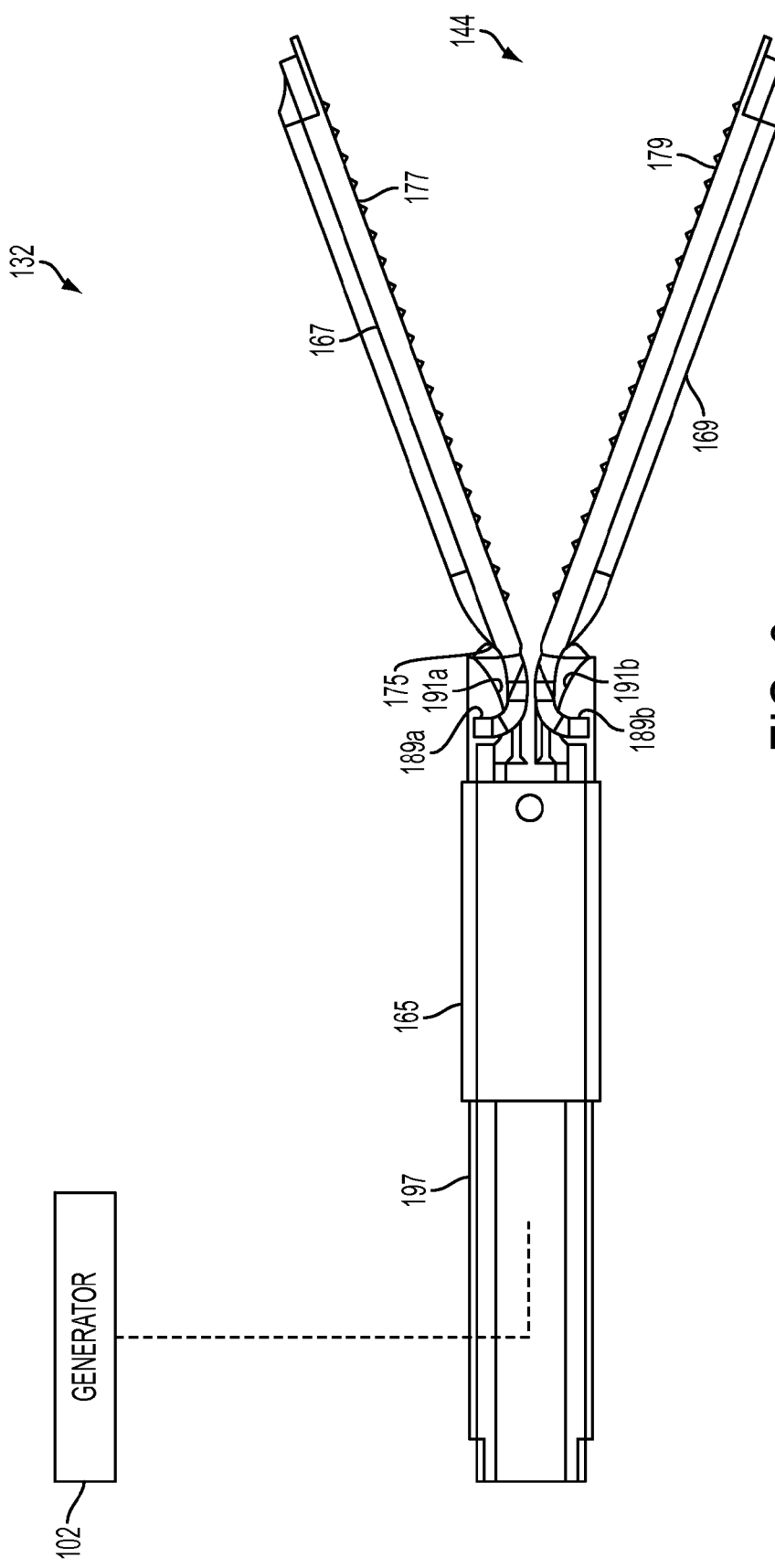
Figure 7:
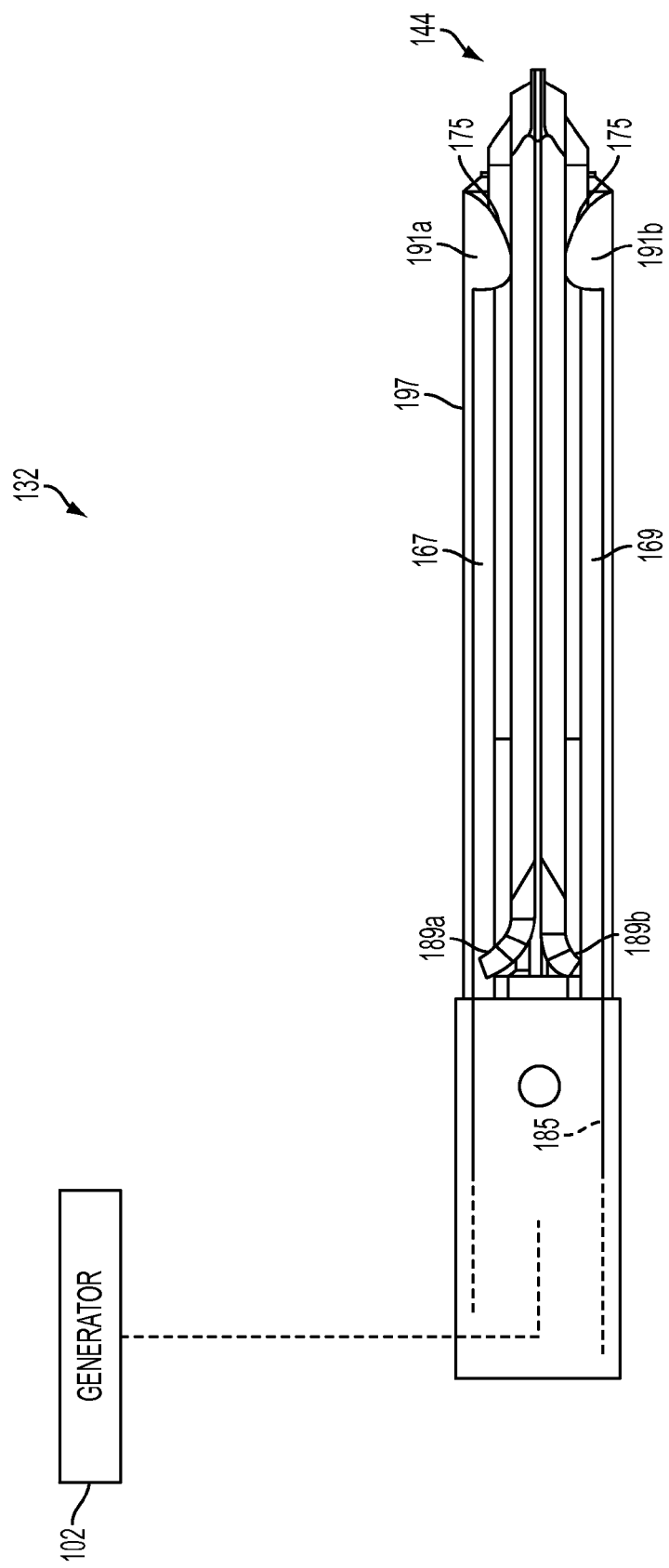

FIGS. 5, 6 and 7 illustrate one embodiment of the end effector 132 shown in FIG. 4. To close the jaws 144 of the end effector 132, a clinician may cause the jaw closure trigger 142 to pivot along arrow 183 from a first position to a second position. This may cause the jaws 144 to open and close according to any suitable method. For example, motion of the jaw closure trigger 142 may, in turn, cause the translating member 173 to translate within a bore 185 of the shaft 165. A distal portion of the translating member 173 may be coupled to a reciprocating member 197 such that distal and proximal motion of the translating member 173 causes corresponding distal and proximal motion of the reciprocating member. The reciprocating member 197 may have shoulder portions 191a, 191b, while the jaw members 167, 169 may have corresponding cam surfaces 189a, 189b. As the reciprocating member 197 is translated distally from the position shown in FIG. 6 to the position shown in FIG. 7, the shoulder portions 191a, 191b may contact the cam surfaces 189a, 189b, causing the jaw members 167, 169 to transition to the closed position. Also, in various embodiments, the blade 175 may be positioned at a distal end of the reciprocating member 197. As the reciprocating member extends to the fully distal position shown in FIG. 7, the blade 175 may be pushed through any tissue present between the jaw members 167, 169, in the process, severing it.

In use, a clinician may place the end effector 132 and close the jaws 144 around a tissue bite to be acted upon, for example, by pivoting the jaw closure trigger 142 along arrow 183 as described. Once the tissue bite is secure between the jaws 144, the clinician may initiate the provision of RF or other electro-surgical energy by the generator 102 and through the electrodes 177, 179. The provision of RF energy may be accomplished in any suitable way. For example, the clinician may activate the foot switch 120 (FIG. 8) of the generator 102 to initiate the provision of RF energy. Also, for example, the hand piece 130 may comprise one or more switches 181 that may be actuated by the clinician to cause the generator 102 to begin providing RF energy. Additionally, in some embodiments, RF energy may be provided based on the position of the jaw closure trigger 142. For example, when the trigger 142 is fully depressed (indicating that the jaws 144 are closed), RF energy may be provided. Also, according to various embodiments, the blade 175 may be advanced during closure of the jaws 144 or may be separately advanced by the clinician after closure of the jaws 144 (e.g., after a RF energy has been applied to the tissue).

FIG. 8 is a diagram of the surgical system 100 of FIG. 1. In various embodiments, the generator 102 may comprise several separate functional elements, such as modules and/or blocks. Different functional elements or modules may be configured for driving the different kinds of surgical devices 104, 106. For example an ultrasonic generator module 108 may drive an ultrasonic device, such as the ultrasonic device 104. An electrosurgery/RF generator module 110 may drive the electrosurgical device 106. For example, the respective modules 108, 110 may generate respective drive signals for driving the surgical devices 104, 106. In various embodiments, the ultrasonic generator module 108 and/or the electrosurgery/RF generator module 110 each may be formed integrally with the generator 102. Alternatively, one or more of the modules 108, 110 may be provided as a separate circuit module electrically coupled to the generator 102. (The modules 108 and 110 are shown in phantom to illustrate this option.) Also, in some embodiments, the electrosurgery/RF generator module 110 may be formed integrally with the ultrasonic generator module 108, or vice versa.

In accordance with the described embodiments, the ultrasonic generator module 108 may produce a drive signal or signals of particular voltages, currents, and frequencies, e.g. 55,500 cycles per second (Hz). The drive signal or signals may be provided to the ultrasonic device 104, and specifically to the transducer 114, which may operate, for example, as described above. In one embodiment, the generator 102 may be configured to produce a drive signal of a particular voltage, current, and/or frequency output signal that can be stepped with high resolution, accuracy, and repeatability.

In accordance with the described embodiments, the electrosurgery/RF generator module 110 may generate a drive signal or signals with output power sufficient to perform bipolar electrosurgery using radio frequency (RF) energy. In bipolar electrosurgery applications, the drive signal may be provided, for example, to the electrodes 177, 179 of the electrosurgical device 106, for example, as described above. Accordingly, the generator 102 may be configured for therapeutic purposes by applying electrical energy to the tissue sufficient for treating the tissue (e.g., coagulation, cauterization, tissue welding, etc.).

In various embodiments, the generator 102 may be configured to provide a charge signal to allow the respective surgical devices to harvest energy for on-board use. The charge signal may be provided by any suitable hardware of the generator 102. For example, in some embodiments, the ultrasonic generator module 108 may provide the charge signal to ultrasonic devices, such as 104 while the electrosurgery/RF module 110 may provide the charge signal to electrosurgical devices, such as 106. The generator 102 may be programmed to configure the signals generated by the respective modules 108, 110 to alternately provide therapeutic drive signals and charge signals, for example, as described herein below. For example, a processor or processors of the generator 102 may receive from a connected surgical device an indication of whether the device is enabled to harvest energy from the generator 102 as well as parameters of the charge signal that the device expects to receive.

The charge signal may have a waveform or frequency that is conducive to efficient charging of the energy harvesting circuit. For example, the energy harvesting circuit may comprise frequency-dependent circuitry such as a filter (e.g., separator circuit 2002 of FIG. 20 below). The charge signal may have a frequency and/or waveform that is synchronous with this frequency-dependent circuitry. Other considerations may include using a high enough frequency to optimize the energy density of the charging waveform while keeping the frequency low enough to provide efficient energy transfer. Also, in some embodiments, the charge signal is bandwidth limited to better operate with rectifiers, such as the rectifiers 1312, 2308, 2402, etc. For example, some rectifier diodes that may be used in the rectifiers described herein have a limited bandwidth due to their junction capacitance. When diodes of this nature are used, the bandwidth of the charge signal may be limited to accommodate them. In some embodiments, the a charge signal may be a direct current (DC) signal and may provide a higher voltage and/or current so as to deliver more power more quickly to charge energy storage associated with the surgical device, as described herein. In some embodiments, the generator 102 may be configured to provide a combined signal that may be divided by the surgical device, for example, as described herein, to yield a charge signal portion for charging the energy storage device and a therapeutic signal portion for deriving the energy element of the device (e.g., electrosurgical electrodes, ultrasonic transducer, etc.).

The generator 102 may comprise an input device 145 located, for example, on a front panel of the generator 102 console. The input device 145 may comprise any suitable device that generates signals suitable for programming the operation of the generator 102. In operation, the user can program or otherwise control operation of the generator 102 using the input device 145. The input device 145 may comprise any suitable device that generates signals that can be used by the generator (e.g., by one or more processors contained in the generator) to control the operation of the generator 102 (e.g., operation of the ultrasonic generator module 108 and/or electrosurgery/RF generator module 110). In various embodiments, the input device 145 includes one or more of buttons, switches, thumbwheels, keyboard, keypad, touch screen monitor, pointing device, remote connection to a general purpose or dedicated computer. In other embodiments, the input device 145 may comprise a suitable user interface, such as one or more user interface screens displayed on a touch screen monitor, for example. Accordingly, by way of the input device 145, the user can set or program various operating parameters of the generator, such as, for example, current (I), voltage (V), frequency (f), and/or period (T) of a drive signal or signals generated by the ultrasonic generator module 108 and/or electrosurgery/RF generator module 110.

The generator 102 may also comprise an output device 147 (FIG. 1) located, for example, on a front panel of the generator 102 console. The output device 147 includes one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). Although certain modules and/or blocks of the generator 102 may be described by way of example, it can be appreciated that a greater or lesser number of modules and/or blocks may be used and still fall within the scope of the embodiments. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one embodiment, the ultrasonic generator drive module 108 and electrosurgery/RF drive module 110 may comprise one or more embedded applications implemented as firmware, software, hardware, or any combination thereof. The modules 108, 110 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one embodiment, the modules 108, 110 comprise a hardware component implemented as a processor for executing program instructions for monitoring various measurable characteristics of the devices 104, 106 and generating a corresponding output drive signal or signals for operating the devices 104, 106. In embodiments in which the generator 102 is used in conjunction with the ultrasonic device 104, the drive signal may drive the ultrasonic transducer 114 in cutting and/or coagulation operating modes. Electrical characteristics of the device 104 and/or tissue may be measured and used to control operational aspects of the generator 102 and/or provided as feedback to the user. In embodiments in which the generator 102 is used in conjunction with the device 106, the drive signal may supply electrical energy (e.g., RF energy) to the end effector 132 in cutting, coagulation and/or desiccation modes. Electrical characteristics of the device 106 and/or tissue may be measured and used to control operational aspects of the generator 102 and/or provided as feedback to the user. In various embodiments, as previously discussed, the hardware components may be implemented as DSP, PLD, ASIC, circuits, and/or registers. In one embodiment, the processor may be configured to store and execute computer software program instructions to generate the step function output signals for driving various components of the devices 104, 106, such as the ultrasonic transducer 114 and the end effectors 126, 132.

In various embodiments, the generator 102 may be capable of communication with a memory circuit of an attached surgical device (e.g., 104, 106) in communication with the generator 102 to determine properties of the surgical device and/or write information to the memory circuit. Device properties stored on the memory circuit may include, for example, a model number, a serial number, a number of operations in which the surgical device has been used, whether and how the device is enabled for energy harvesting, and/or any other type of information. In some embodiments, the generator 102 may also write to the memory circuit, for example, to update a number of times that the surgical device has been used, record other information about the use of the device, etc. The memory circuit itself may comprise a digital memory device or other data circuit and/or a series of switches, diodes, resistors, etc. assuming a state that may be sensed by the generator 102 to infer a property of the surgical device. The memory circuit may be associated with the surgical device. For example, the memory circuit may be physically positioned within the surgical device, within a cable connecting the surgical device to the generator 102, within an adapter for connecting the cable to the generator 102 or surgical device, within a companion piece of hardware positioned between the generator 102 and the surgical device, etc.

Figure 9:
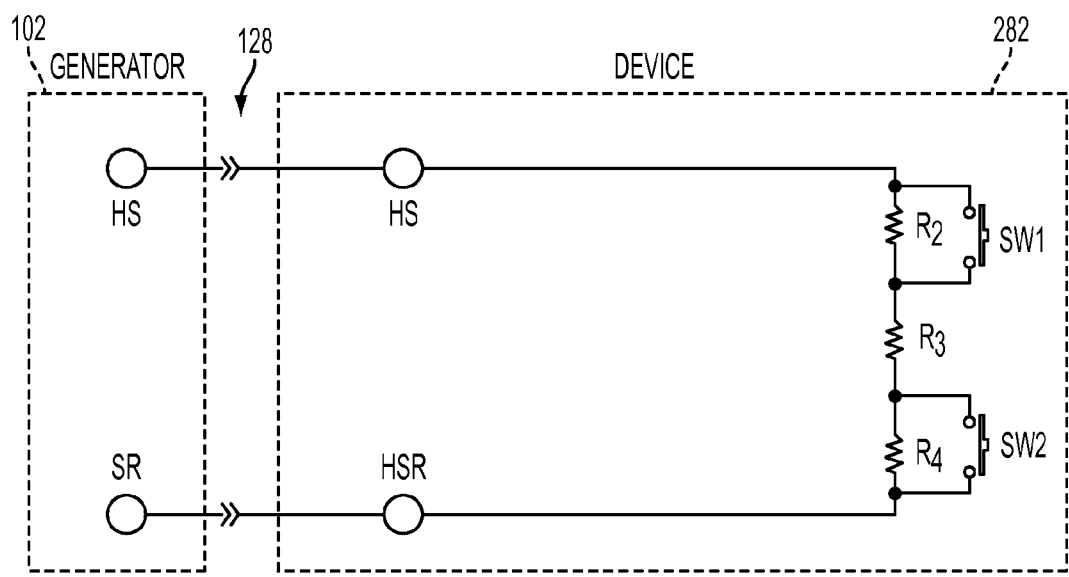
FIGS. 9 and 10 illustrate embodiments of memory circuits for surgical devices configured to encode device properties on an interrogation signal.
Figure 10:
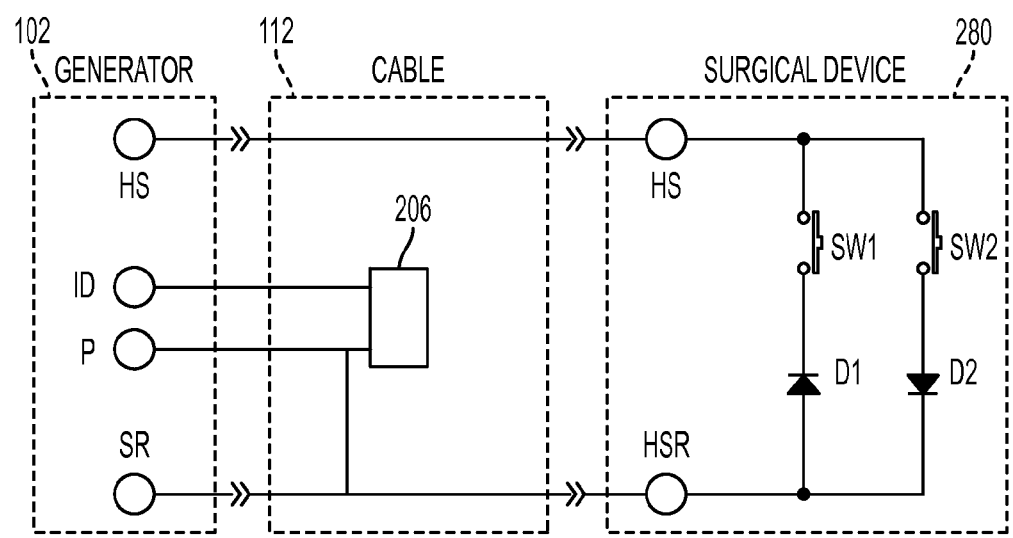

In some embodiments, the generator 102 creates an interrogation signal and provides the interrogation signal to the surgical device. For example, the interrogation signal may be provided via a conductive pair in a cable that connects the generator 102 to the surgical device. The memory circuit at the device may act on the interrogation signal to encode device properties on the interrogation signal. The generator 102 may monitor the interrogation signal to discern the encoded properties. FIGS. 9 and 10 illustrate embodiments of memory circuits 282, 280 for surgical devices configured to encode device properties on an interrogation signal. The memory circuits 282, 280 of FIGS. 9 and 10 may modify characteristics of an interrogation signal transmitted by the generator 102. The characteristics of the interrogation signal, which may uniquely indicate the state or configuration of the control circuit, can be discerned by the generator 102 and used, for example, to control aspects of its operation. The memory circuits 282, 280 of FIGS. 9 and 10 may be utilized in any kind of surgical device including, for example, an ultrasonic surgical device such as 104 and/or an electrosurgical device, such as 106.

Referring to FIG. 9, memory circuit 282 may be connected to the generator 102 to receive an interrogation signal (e.g., a bipolar interrogation signal at 2 kHz). The memory circuit 282 may comprise series-connected resistors R2, R3 and R4, with switches SW1 and SW2 connected across R2 and R4, respectively. The generator 102 may apply the interrogation signal across at least one of the series-connected resistors to generate a voltage drop across the memory circuit 282. The state of the switches SW1 and SW2 may determine the characteristics of the interrogation signal and, therefore, also indicate properties of the surgical device. For example, when both SW1 and SW2 are open, the voltage drop may be determined by R2, R3 and R4. When SW1 is closed and SW2 is open, the voltage drop may be determined by R3 and R4. When SW1 is open and SW2 is closed, the voltage drop may be determined by R2 and R3. When both SW1 and SW2 are closed, the voltage drop may be determined by R3. Accordingly, based on the voltage drop across the memory circuit 282 the state or configuration of the memory circuit 282 may be discerned by the generator 102.

Referring to FIG. 10, the memory circuit 280 may be coupled to the generator 102 to receive an interrogation signal (e.g., a bipolar interrogation signal at 2 kHz). The memory circuit 280 may comprise a first switch SW1 in series with a first diode D1 to define a first branch, and a second switch SW2 in series with a second diode D2 to define a second branch. The first and second branches may be connected in parallel such that the forward conduction direction of D2 is opposite that of D1. The interrogation signal may be applied across both branches. Again, the state of the switches SW1, SW2 may determine characteristics of the interrogation signal. When both SW1 and SW2 are open, the memory circuit 280 may define an open circuit. When SW1 is closed and SW2 is open, the interrogation signal may undergo half-wave rectification in a first direction (e.g., positive half of interrogation signal blocked). When SW1 is open and SW2 is closed, the interrogation signal may undergo half-wave rectification in a second direction (e.g., negative half of interrogation signal blocked). When both SW1 and SW2 are closed, no rectification may occur. Accordingly, based on the different characteristics of the interrogation signal corresponding to the different states of SW1 and SW2, the state or configuration of the memory circuit 280 may be discerned by the generator 102 based on a voltage signal appearing across the inputs of the memory circuit 280, as measured by the generator 102.

In addition to or instead of the switches SW1, SW2, various surgical device memory circuits may also include digital data storage elements. For example, referring to FIG. 14, the cable 112 is shown to comprise a digital data storage element 206. The digital data storage element 206 may comprise, for example, a non-volatile storage device, such as an EEPROM device. The generator 102 may exchange information with the digital data storage element 206. Such information may be specific to a surgical device integral with, or configured for use with, the cable 112 and may comprise, for example, a model number, a serial number, a number of operations in which the surgical device has been used, whether and how the device is configured for information harvesting, and/or any other type of information. Information may also be communicated from the generator 102 to the digital data storage element 206 for storage therein, as discussed above in connection with FIG. 10.

Figure 11:
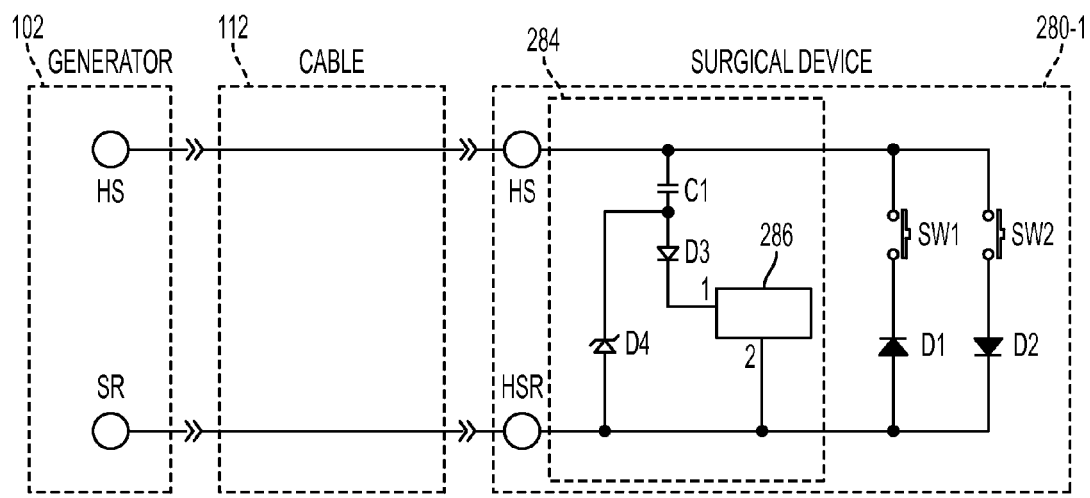
FIG. 11 illustrates one embodiment of a memory circuit comprising a digital data storage element.

In certain embodiments, the digital data circuits, such as 206, may be positioned in the surgical device itself and/or in an adaptor for interfacing a specific surgical device type or model with the generator 102. For example, FIG. 11 illustrates one embodiment of a memory circuit 280-1 comprising a digital data storage circuit 284 comprising a digital data storage element 286. In certain embodiments, the digital data storage element 286, and possibly other components of the memory circuit 284, may be contained in the device and/or cable 112, with other components of the memory circuit 280-1 (e.g., SW1, SW2, D1, D2, D3, D4, C1) being contained in the hand piece (e.g., hand piece 116). In certain embodiments, the data storage element 286 may be a single-wire bus device (e.g., a single-wire protocol EEPROM), or other single-wire protocol or local interconnect network (LIN) protocol device. In one embodiment, for example, the data storage element 286 may comprise a Maxim DS28EC20 1-Wire 0 EEPROM, available from Maxim Integrated Products, Inc., Sunnyvale, Calif.

In certain embodiments, the generator 102 may be configured to communicate with the digital data circuit 284, and, in particular, with the digital data storage element 286, via the conductive pair of the cable 112. In particular, the frequency band of the communication protocol used to communicate with the memory circuit 284 may be higher than the frequency band of the interrogation signal. In certain embodiments, for example, the frequency of the communication protocol for the data storage element 286 may be, for example, 200 kHz or a significantly higher frequency, whereas the frequency of the interrogation signal used to determine the different states of SW1 and SW2 may be, for example, 2 kHz. Accordingly, the value of capacitor C1 of the digital data circuit 284 may be selected such that the digital data storage element 286 is "hidden" from the relatively low frequency of the interrogation signal while allowing the generator 102 to communicate with the data storage element 286 at the higher frequency of the communication protocol. A series diode D3 may protect the data storage element 286 from negative cycles of the interrogation signal, and a parallel Zener diode D4 may limit the voltage supplied to the data storage element 286 to a suitable operating range (e.g., 3.3-5V). When in the forward conduction mode, D4 may also clamp negative cycles of the interrogation signal to ground. In some embodiments, the generator 102 may be configured to write to the digital data storage element 286. For example, the generator 102 may write an updated number of operations in which the device has been used and/or dates and/or times of its usage. Additional examples of suitable memory circuits that may be used with surgical devices are disclosed in United States Patent Application Publication No. 2012-0265196, filed on Apr. 16, 2012, and in United States Patent Application Publication No. 2011-0087212, filed on Oct. 1, 2010, both incorporated herein by reference in their entireties.

Figure 12:
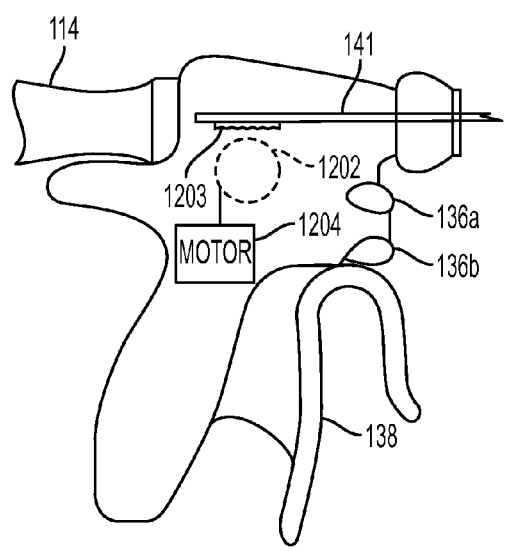
FIG. 12 illustrates one embodiment of the ultrasonic instrument of FIG. 1 with the hand piece comprising a motor.

In some example embodiments, either of the surgical devices 104, 106 may have respective end effectors that are operated by a motor or according to a motor assist system. For example, FIG. 12 illustrates one embodiment of the instrument 104 with the hand piece 116 comprising a motor 1204. The jaw closure member 141 is shown with a rack gear 1203 attached thereto. A gear 1202 is positioned to contact the rack gear 1203 such that rotation of the gear 1202 causes linear translation of the rack gear 1203 and jaw closure member 141. The motor 1204 may be coupled to the gear 1202 such that rotation of the motor 1204 causes rotation of the gear 1202 and, consequently, linear translation of the jaw closure member 141 along alternately distal and proximal directions depending on the direction of rotation of the motor 1204. The motor 1204 may be configured to be actuated when the clinician actuates the jaw closure trigger 138. The jaw closure trigger 138 may be mechanically coupled to the jaw closure member 141 such that the motor 1204 provides an "assist" to the closing of the clamp arm 155. In some embodiments, the jaw closure trigger 138 is not mechanically coupled to the jaw closure member 141 such that most or all of the power provided to close the clamp arm 155 is provided by the motor 1204. Although the motor 1204 is illustrated in the context of the ultrasonic surgical device 104, it will be appreciated that a similar arrangement may be created with respect to devices, such as the electrosurgical device 106. For example, the rack gear 1203 may be coupled to the translating member 173 to close the jaw members 167, 169 and/or drive the blade 175.

Figure 13:
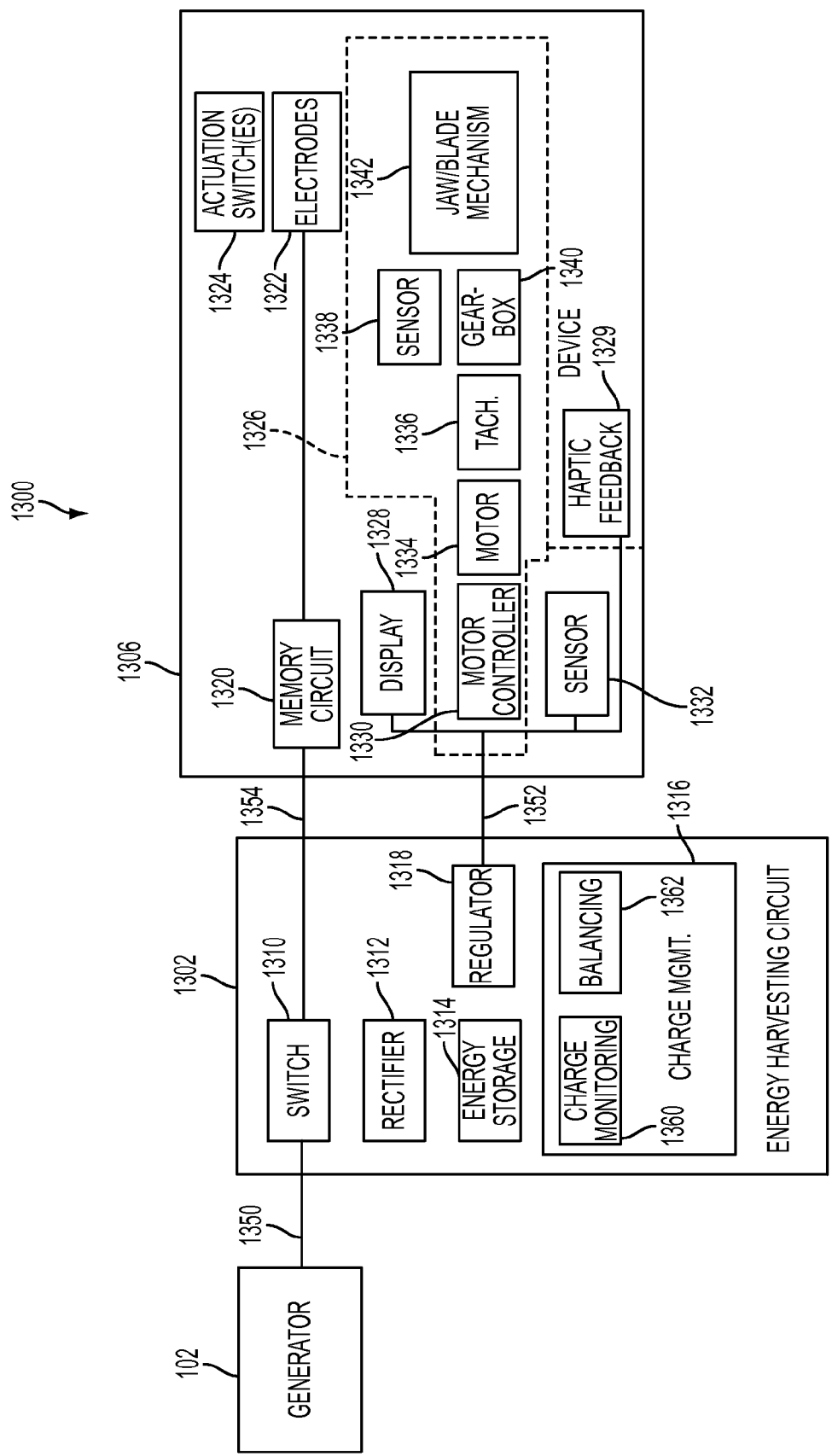
FIG. 13 is a block diagram illustrating one embodiment of a surgical system configured for harvesting energy provided by the generator.

FIG. 13 is a block diagram illustrating one embodiment of a surgical system 1300 configured for harvesting energy provided by the generator. The system 1300 comprises a generator 102, an energy harvesting circuit, and an electrosurgical device 1306. The generator 102 may be configured to alternately provide a therapeutic drive signal and a charge signal. The therapeutic drive signal may be provided to a pair of electrodes 1322, similar to the electrodes 179, 177 described herein, to treat tissue. The charge signal may be utilized to charge an energy storage device 1314 that may be, for example, a capacitor (e.g., a super capacitor, or high-voltage electrolytic capacitor) or any suitable type of battery (e.g., a Lithium Ion or Li-ion battery). As used herein, the term battery shall refer to one or more energy storage cells utilized to store electrical energy. The energy storage device 1314 may be subsequently used to power various components of the surgical device 1306 including, for example, one or more displays 1328, one or more mechanical drive trains 1326, one or more sensors 1332, etc. In some embodiments utilizing a generator 102 configured for both ultrasonic and electrosurgical devices, the charge signal may simply be the standard electrosurgical therapeutic drive signal. For example, an electrosurgical drive signal may be suited to energy harvesting because it may have a higher frequency and a higher output current capability relative to an ultrasonic drive signal. Accordingly, in some embodiments of the surgical system 1300 with the electrosurgical device (1306) there may be no difference or minimal differences between the therapeutic drive signal and the charge signal. Similarly, in some embodiments of the surgical system 1300 with an ultrasonic device 1304 (FIG. 14), the therapeutic drive signal may be a form of the generator's ultrasonic drive signal while the charge signal may be a form of the generator's electrosurgical therapeutic drive signal.

The energy harvesting circuit 1302 may include the energy storage device 1314 as well as various components for charging, discharging and conditioning the energy storage device 1314. The energy harvesting circuit 1302 is shown in FIG. 13 as a distinct component of the surgical system. It may, however, be physically embodied in any suitable manner. For example, the energy harvesting circuit 1302 may be incorporated into the surgical device 1306 itself, for example, within the hand piece assembly such as 130 described above. Also, in some embodiments, the energy harvesting circuit 1302 may be included as self-contained box that may, for example, be placed on a table or other location in the surgical environment, such as the break-out box 149 of FIG. 1. For example, the self-contained box may receive the therapeutic drive signal and charge signal from the generator 102 and provide its outputs to the surgical device 1306 via additional connections. In some embodiments, some or all of the components and functionality of the energy harvesting circuit 1302 may be incorporated into the generator 102 itself.

The energy harvesting circuit 1302 may receive a drive signal from the generator 102, for example, via a surgical generator connection 1350. The connection 1350 may be a multi-conductor cable, such as 112 and 128 described above. The drive signal, in various embodiments, is provided to a switch 1310. The switch 1310 may alternately direct the drive signal to the electrodes of the surgical device 1306 and/or to the energy storage device 1314. For example, when the generator 102 provides a therapeutic drive signal, the switch 1310 may be configured to direct the therapeutic drive signal to the surgical device via a connection 1354. The connection 1354 may also be a multi-conductor cable, for example, similar to the cables 112 and 128 above. When the generator 102 provides a charge signal, the switch 1310 may be configured to direct the charge signal to the energy storage device 1314.

The charge signal, as directed by the switch 1310, may be provided to the energy storage device 1314 via one or more additional components of the energy harvesting circuit 1302. For example, although the charge signal may be a direct current signal suitable for charging the energy storage device 1314, in some embodiments, the charge signal will be an alternating current signal. For example, the generator 102 may be configured to provide alternating current therapeutic drive signals. Accordingly, utilizing an alternating current charge signal may, in some embodiments, avoid the necessity of hardware changes to the generator 102. Also, in some embodiments, an alternating current charge signal may be desirable for other reasons. In various embodiments, the switch 1310 may comprise a relay or other mechanical switch in addition to or instead of a transistor or other soft switch. This may minimize the risk that the charge signal will be provided to the electrodes 1322 and, therefore, to the patient. The state of the charge switch 1310 may be controlled in any suitable manner. For example, in some embodiments, the charge switch 1310 may comprise a control circuit. The control circuit may be configured to switch the charge switch 1310 based on characteristics of the received drive signal. For example, when the drive signal is a therapeutic drive signal, the switch 1310 may be set to the energy storage device 1314 and when the drive signal is a charge signal, the switch 1310 may be set to the device 1306. Also, in some embodiments, the state of the charge switch 1310 may be controlled by a microprocessor or other suitable component or functionality of the charge management circuit 1316, described in more detail herein below.

When the charge signal is an alternating current signal, the energy harvesting circuit 1302 may comprise a rectifier 1312 to convert the charge signal from alternating current to direct current. The resulting direct current charge signal may be provided to the energy storage device 1314 for charging. The charge management circuit 1316 may provide various functionalities for managing the charging (and discharging) of the energy storage device 1314. For example, the charge management circuit 1316 may comprise a charge monitoring module 1360. The charge monitoring module 1360 may monitor the level of charge on the energy storage device 1314. In some embodiments, the charge monitoring module 1360 may also generate a signal indicating a level of charge for the energy storage device 1314. For example, the charge monitoring module may provide a binary signal indicating whether the energy storage device 1314 has reached a threshold level of charge. For example, the signal may be asserted when the energy storage device 1314 comprises enough charge to complete a predetermined number of firings of the device 1306 (e.g., one firing). In some embodiments, the charge monitoring module 1360 may comprise a comparator tied to a reference voltage. When the voltage level of the energy storage device 1314 exceeds the reference voltage, the output of the comparator may be pulled high, generating the signal. The signal may be provided to a light emitting diode (LED) or other display device. Also, in some embodiments, the charge monitoring module may generate a signal indicating a level of charge on the device 1314. The level may be expressed in any suitable manner including, for example, a voltage drop across the device, a percentage of total charge, a number of device firings available, etc. In embodiments where the energy storage device comprises one or more batteries, such as Li-ion batteries, the charge monitoring module 1360 may include additional functionality for quantifying the charge provided to the battery. For example, some embodiments may utilize an available battery fuel gauge integrated circuit (IC) such as the BQ2754DRZT-G1 available fro TEXAS INSTRUMENTS.

In embodiments where the energy storage device 1314 comprises a bank of super capacitors or high-voltage electrolytic capacitors, the charge management circuit 1316 may comprise a balancing module 1360 for balancing the charge across each of the capacitors during charging so as to avoid overvoltage damage to the individual capacitors. It will be appreciated that the charge management circuit 1316 may be configured to perform various other functionalities in the system 1300. For example, in some embodiments, the charge management circuit 1316 is configured to provide other functionality related to the charging or discharging of the energy storage 1314. For example, the charge management circuit may condition the charge signal. In some embodiments, some functions of the charge management circuit 1316 and the rectifier 1312 may be combined into a single circuit, for example, utilizing a charge management IC, such as the BQ24600RVAT management chip available from TEXAS INSTRUMENTS.

The energy storage device 1314 may provide power to various components of the surgical device 1306. For example, the energy storage device 1314 may be coupled to components of the surgical device 1306 via a regulator 1318. The regulator 1318 may be configured according to any known linear and/or switching regulator design to condition energy discharged by the energy storage device 1314 to provide power to the surgical device 1306. The regulator 1318 may provide a single output voltage. In some embodiments, the output voltage provided by the regulator 1318 is configurable between two alternate values (e.g., 12 volts or 15 volts) for example by a switch and/or jumper. Also, in some embodiments, the regulator 1318 is configured to simultaneously provide two output voltages. For example, the regulator 1318 may provide a power signal for driving the mechanic drive train 1326 and other powered components of the surgical device 1306 as well as a lower logic signal for powering displays, such as 1328, sensors, such as 1332 and 1338 or other similar components. The regulator may provide the one or more output voltages to the surgical device 1306 (e.g., the load components thereof) via a supply line and/or bus 1352. When the energy harvesting circuit 1302 is integral to the surgical device 1306, the supply line 1352 may also be integral. Alternatively, when the energy harvesting circuit 1302 is external to the surgical device 1306, the supply line 1352 may comprise one or more conductor pairs positioned between the components 1302, 1306. For example, the additional conductor lines may be included in a single cable that also houses conductors for the connection 1350 described herein above.

Referring now to the device 1306, when the drive signal is a therapeutic drive signal and the switch 1310 is configured to provide the therapeutic drive signal via the connection 1320, the therapeutic drive signal may be, in turn, provided to the electrodes 1322. The clinician may initiate actuation of the therapeutic drive signal to the electrodes 1322, for example, utilizing one or more actuation switches 1324, which may be manifested on the device 1306, for example, as switch 181. Actuation switches 1324 may comprise any switch on the device 1306 by which the clinician indicates an operation to be performed by the device including, for example, jaw closer triggers 138, 142, buttons 136*a*, 136*b*, 136*c*, switch 181, etc. For example, actuation of the switch 181 by the clinician may cause an actuation signal that may be communicated to the generator 102 and/or a component of the device 1306 itself. The actuation signal may be provided to the generator 102 in any suitable manner including, for example, via the connections 1350 and 1352 and/or as described herein with respect to FIG. 13A. For example, the generator 102 may be configured to not provide any drive signal and/or to provide a charging drive signal until the actuation signal is received. When the actuation signal is received, the generator 102 may provide the therapeutic drive signal. Also, in some embodiments, the actuation switches 1324 may comprise more than one switch and/or a switch with more than one position. In this case, the resulting actuation signal may have multiple states. The generator 102 may modify a mode of the drive signal, for example, depending on the state of the actuation signal. In some embodiments, the actuation signal may be received by a component of the device 1306 itself such as, for example, the charge management circuit 1316. The charge management circuit 1316 may separately communicate with the generator 102 to configure the received drive signal and/or may manipulate the switch 1310 to ensure that the drive signal is provided to the electrodes 1322 only when called for by the clinician.

The device 1306 may also comprise a memory circuit 1320. The memory circuit 1320 may be configured in a manner similar to that described herein above with respect to FIGS. 9-11. For example, the memory circuit 1306 may store information describing the surgical device 1306 and/or a state of the surgical device 1306. In some embodiments, the memory circuit 1320 may indicate to the generator 102 that the surgical device 1306 is configured for energy harvesting, which may signal to the generator 102 to provide a charge signal. The memory circuit 1320 may also comprise data indicating the form of the charging and various control information such as, for example, when the device 1306 expects to receive the charge signal, etc. As described herein above, information may be encoded in the memory circuit 1320 in any suitable manner including, for example, by the position of switches and/or utilizing a digital memory device such as electrically erasable read only memory (ROM) or random access memory (RAM). In some embodiments, the generator 102 may comprise a capacity to write to the memory circuit. For example, the generator 102 (and/or other control component at the device 106) may indicate various data about how the device has been used (a number of firings, a number of charge cycles on the energy harvesting circuit 1302, etc.). Additional embodiments showing configurations for communication between the device 1306 and the generator 102 are described herein with respect to FIG. 13A.

As illustrated, the electrosurgical device 1306 may comprise various powered components that may draw power from the energy harvesting circuit 1302. For example, the electrosurgical device 1306 may comprise one or more displays 1328. The display 1328 may be any suitable type of display such as, for example, in indicator light or set of indicator lights, a liquid crystal or other suitable display, etc. In some embodiments, the display 1328 is in communication with the memory circuit 1320 or other suitable data storage to receive and display data about how the device has been used. In some embodiments, the display 1328 is in communication with the charge management circuit 1316 or other suitable component to receive an indication of the charge state of the energy storage device 1314. The display 1328 may indicate the charge state in any suitable manner including, for example, as a bar or in numerical form. Either representation may express the charge state in terms of output voltage, portion or percentage of charge available, etc. In some embodiments, the device 1304, 1306 may comprise a haptic feedback device 1329. For example, the haptic feedback device 1329 may be configured to provide haptic feedback to the clinician using the device. For example, the haptic feedback device may comprise a motor configured to create a vibration in the device, a motor configured to provide force-feedback on one or more of the actuation switches 1324, etc. In some embodiments, haptic feedback device 1329 may be utilized to indicate that the energy storage device 1314 is either charged and/or charged sufficiently to perform a firing of the instrument. The electrosurgical device 1306 may also comprise one or more sensors 1332 powered by the energy storage device 1314. The sensors may be configured to sense various properties of the device 1306 and/or the patient or tissue being treated. For example, in some embodiments the sensor 1332 may comprise electrodes, such as electrodes 157, 159, for measuring the electrical impedance of a tissue bite. Power to the electrodes 157, 159 may be provided by the energy harvesting circuit 1302.

In various embodiments, the powered components may also comprise a mechanical drive train 1326. The mechanical drive train 1326 may comprise one or more motors 1334 and may be configured to perform one or more mechanical tasks in the device 1306. For example, the mechanical drive train 1326 may be configured to actuate the jaw/blade mechanism of the device 1306, for example, in a manner similar to that described above with respect to FIG. 12. In some embodiments, a motor 1334 for this purpose may be configured to output 150 joules (J) per cycle. Also, in some embodiments, the drive train 1326 may be configured to articulate a jointed shaft 124, 165.

The drive train 1326 may comprise various components suitable for performing the described tasks. For example, the drive train 1326 may comprise a motor controller 1330 and motor 1334. The motor controller 1330 may receive a signal from one of the actuation switches 1324 when the clinician desires to execute a power or power-assisted function of the device. For example, when the power or power-assisted function is a closing of the jaws and advancement of the blade mechanism, the signal may be received from the jaw closure trigger 142. In response, the motor controller 1330 may instruct the motor 1334 to make appropriate motions to execute the function. The motor 1334 may be any suitable type of motor. For example, in some embodiments, the motor 1334 is a stepper motor configured to run on 12 and/or 15 volts DC. In some embodiments, the drive train 1326 comprises a tachometer 1336 for measuring a rate of rotation of the motor 1334. The tachometer 1336 may be implemented, for example, utilizing a rotary or other suitable type of encoder. The tachometer 1336, for example, may provide a signal to the display 1328 for display to the clinician and/or to the memory circuit 1320 for storage and later retrieval. The motor 1334 may be in mechanical communication with the jaw/blade mechanism 1342 via a gearbox 1340. One example configuration of the gearbox 1340 is described above with respect to FIG. 12. For example, the gearbox 1340 may comprise gears similar to the gears 1202, 1203 described therein. The drive train 1326 may comprise one or more sensors 1338 to indicate a position of the jaw/blade mechanism 1342. For example, the sensor 1338 may comprise a proximity sensor positioned on the translating member 173 to measure a position of the translating member 173 relative to the shaft. Also, in some embodiments, the sensor 1338 comprises a proximity and/or contact sensor to sense a position of the jaw members 167, 169 relative to one another. Also, in some embodiments, the sensor 1338 comprises an end-of-stroke sensor positioned to sense the jaw members 167, 169 and/or the translating member at the end of their respective strokes. Outputs from the sensor or sensors 1338 may be provided, for example, to the motor controller 1330 which may, in accordance, drive the motor 1334.

Figure 13A:
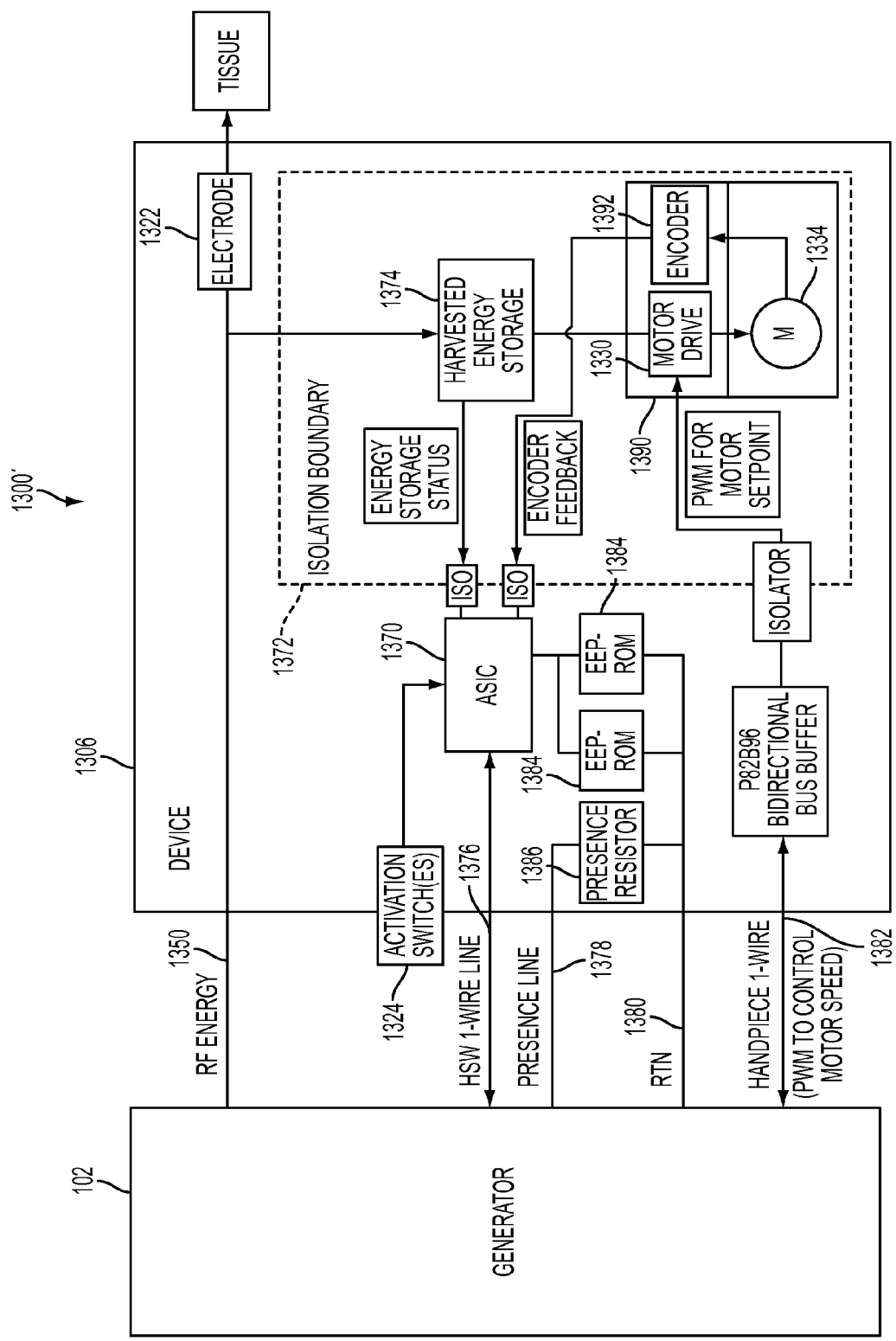
FIG. 13A is a block diagram of another embodiment of a surgical system illustrating additional methods of communication between the device and the generator.

FIG. 13A is a block diagram of another embodiment of a surgical system 1300' illustrating additional methods of communication between the device 1306 and the generator 102. In the surgical system 1300', the device 1306, optionally, comprises additional communication lines to the generator including, for example, a communication line 1376, a presence line 1378, a signal return line 1380, and a 1-wire line 1382. The additional communication lines, for example, may be physically consolidated with the line 1350, for example, in a common cable such as 112, 128 described herein above. Some or all of the signal communication between the device 1306 and the generator 102 may be managed through an application specific integrated circuit (ASIC) 1370. The ASIC 1370 may be configured to store and transmit to the generator 102 a number of inputs from the device 1306. Communications between the ASIC 1370 and the generator 102 may be conducted over the communication line 1376 and signal ground 1380. The inputs may be received from various components of the device 1306. For example, the ASIC 1370 may be in communication with one or more EEPROMS or other digital memory devices 1384. The digital memory devices 1384 may store various information about the device 1306 such as, for example, a model number, a serial number, a number of operations in which the surgical device has been used, whether and how the device is configured for information harvesting, and/or any other type of information. The ASIC 1370 may also receive inputs from the various activation switches 1324. For example, as described herein, the activation switches 1324 may include a switch for initiating the delivery of electrosurgical energy, a switch for initiating the clamping and/or cutting of tissue, etc.

In some embodiments, the ASIC 1370 may also receive input signals from the harvested energy storage 1374 and drive train 1390. The harvested energy storage 1374 may comprise some or all of the components described herein above with respect to the energy harvesting circuit 1302. For example, the harvested energy storage 1374 may comprise an energy storage device, similar to 1314 and a charge management circuit, similar to 1316. The energy harvesting circuit 1302 may provide one or more inputs to the ASIC 1370 (and ultimately to the generator 102) that indicate a status of the energy storage device including, for example, a level of charge, a voltage level, a number of charge cycles performed, or any other suitable information about the energy storage device. The drive train 1390 may also provide an input to the ASIC 1370 indicating its status. For example, an encoder 1392 may provide an input to the ASIC 1370 that indicates the position of the motor 1334 (and thereby, a position of the jaw/blade mechanism 1342). In some embodiments, the encoder 1392 is replaced and/or supplemented by the tachometer 1336 shown in FIG. 13.

In some embodiments, the motor controller 1330 may have a separate control line 1382 to the generator 102 via a bidirectional buffer. The control line 1382 may be utilized to control the pulse width modulation of the control signal to the motor. For example, in some embodiments, control of the motor or other device component may be implemented at the generator rather than local to the device. This may provide advantages, for example, when the motor or other device component is controlled based on a parameter measured at the generator. For example, when the motor 1334 is advancing the jaw/blade mechanism 1342, the advance of the blade may be timed based on a tissue property, such as impedance. In some embodiments, a presence resistor or network of resistors 1386 may also be in communication with the generator 102 via a separate conductor 1378. The value of the resistor or resistor network 1386 may indicate the device 1306 and/or other information about the device, for example, similar to the resistor networks described herein with respect to FIGS. 9-11. As illustrated in FIG. 13A, some components of the device 1306 may be electrically isolated from the generator 102 within an isolation boundary 1372. Signal lines crossing the isolation boundary may utilize a transformer or other suitable isolation component to maintain isolation. Additionally, in some embodiments, it will be appreciated that the communication lines 1376, 1378 and/or 1382 may be replaced by a wireless communication system for communicating between the generator 102 and the device 1306.

Figure 14:
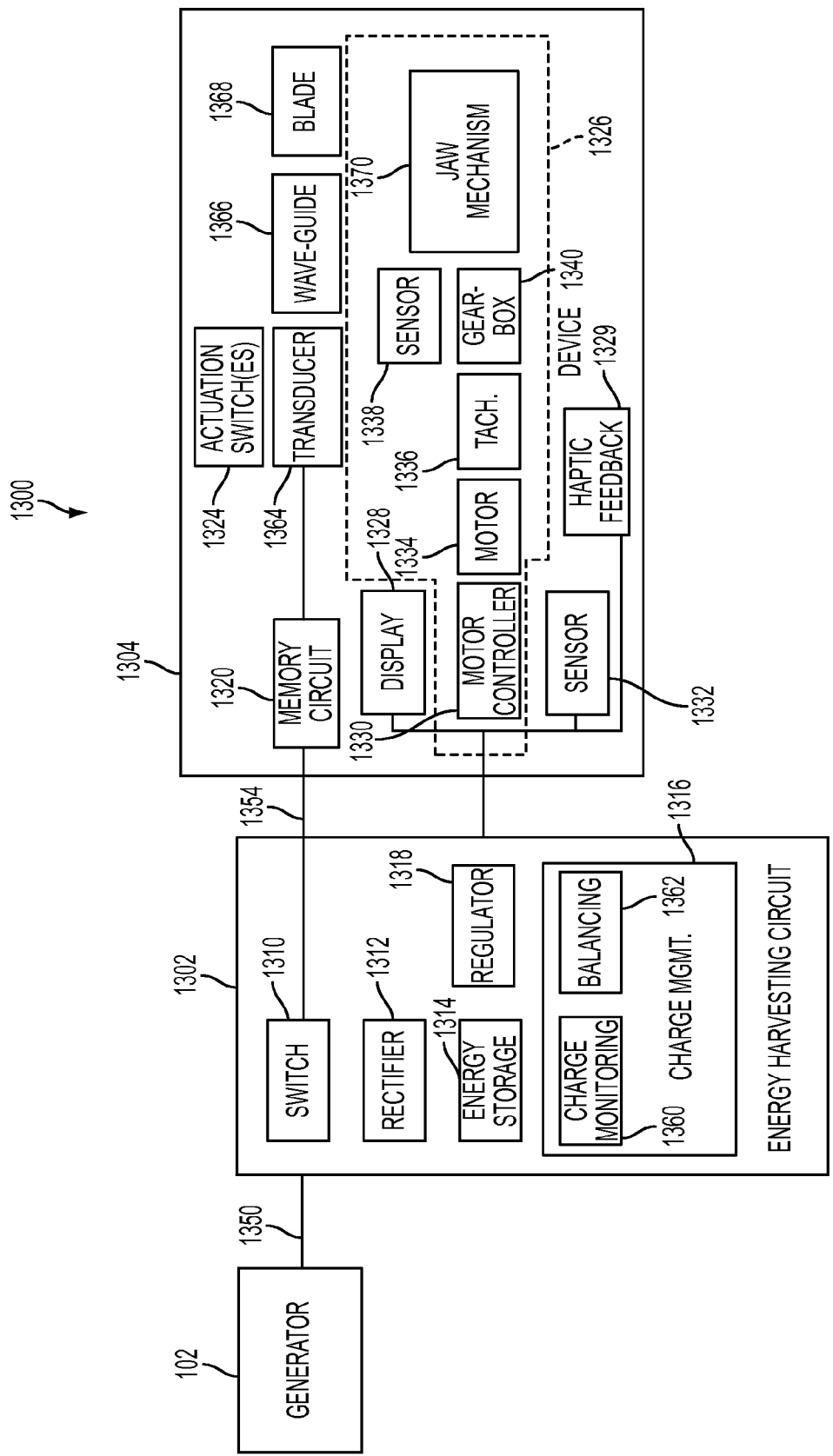
FIG. 14 is a block diagram illustrating one embodiment of a surgical system configured for harvesting energy provided by the generator and utilizing the energy in an ultrasonic surgical device.

FIG. 14 is a block diagram illustrating one embodiment of a surgical system 1300 configured for harvesting energy provided by the generator 102 and utilizing the energy in an ultrasonic surgical device 1304. The generator 102 and energy harvesting circuit 1302 may operate in a manner similar to that described herein with respect to FIG. 13. In place of the electrodes 1322 of the electrosurgical device 1306, the ultrasonic device 1304 may comprise a transducer 1364, waveguide 1366 and blade 1368. The transducer 1364 may receive a therapeutic drive signal in a manner similar to that described above with respect to the electrodes 1322. Additionally, some ultrasonic devices may omit a blade 151 and may, instead, comprise a jaw mechanism 1370 for closing the clamp arm, such as clamp arm 155.

Although the energy harvesting embodiments shown above are described with reference to a bi-polar electrosurgical device and an ultrasonic electrosurgical device, it will be appreciated that the energy harvesting arrangements described herein may be utilized with any surgical device that is used in conjunction with a surgical generator 102, including surgical devices with different energy elements. For example, a surgical device for use with the energy harvesting circuit 1302 may be a monopolar surgical device comprising a single electrode. The single electrode may be positioned on a member of the jaws 140, or any other feature of the end effector 126. Also, for example, the energy harvesting circuit 1302 described herein may be used in conjunction with a cautery end effector comprising a heating element, a laser end effector, etc. In devices that do not typically utilize a bi-polar connection to the generator 102 (e.g., monopolar electrosurgical devices), the charge signal may be generated in any suitable manner. For example, the devices may utilize a bi-polar connection to the generator with the monopolar drive signal derived at the energy harvesting circuit 1302. Also, in some embodiments, a monopolar drive signal may be utilized by the energy harvesting circuit 1302. For example, the energy harvesting circuit may comprise a transformer to generate a bi-polar charge signal from a monopolar signal received from the generator 102.

Figure 15:
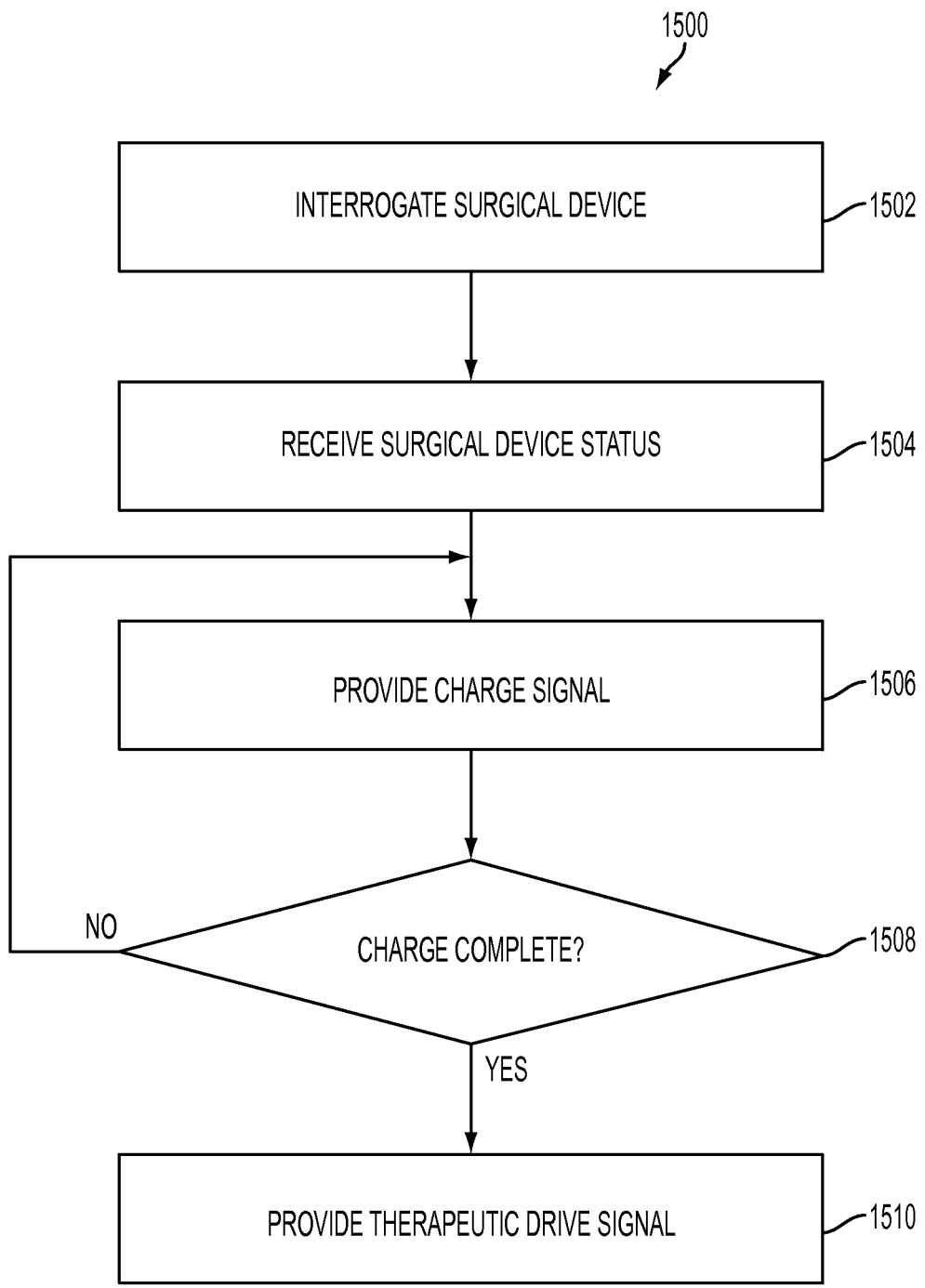
FIG. 15 is a flow chart illustrating one embodiment of a process flow that may be executed by the generator to provide a charge signal to a surgical device.

FIG. 15 is a flow chart illustrating one embodiment of a process flow 1500 that may be executed by the generator 102 to provide a charge signal to a surgical device, such as one of the surgical devices 1304, 1306 described herein. At 1502, the generator may interrogate the surgical device, for example, by providing an interrogation signal. For example, the interrogation signal may be provided when the device is first coupled to the generator 102 and/or when the clinician first activates an actuation switch 1324 or other input of the device. In response to the interrogation signal, the surgical device (e.g., via the memory circuit 1320) may provide a status of the surgical device. The status of the surgical device may indicate any suitable information about the device, for example, as described herein. The status of the surgical device may include an indication of whether the device is configured for energy harvesting. The generator 102 may receive the status of the surgical device at 1504. For example, the status may be received as a modification to the characteristics of the interrogation signal and/or by communications with a digital memory device, for example, as described herein with reference to FIGS. 9-11.

In instances where the surgical device is not configured for energy harvesting, the generator 102 may provide a therapeutic drive signal, for example, in response to actuation of an actuation switch. When the device is configured for energy harvesting, the generator may provide a charge signal at 1506. The surgical device may utilize the charge signal, as described herein, to charge the energy storage device 1314. At 1508, the generator 102 may determine whether the charge is complete. The generator 102 may determine whether the charge is complete in any suitable manner. For example, in some embodiments, the device may provide a signal indicating that the charge is complete. Also, in some embodiments, when the charge is complete, the device may be configured to modify the state of the switch 1310. For example, the switch 1310 may have a third state where the generator 102 is not in electrical communication with either the energy storage device 1314 or the electrodes 1322 (in an electrosurgical device 1306) or the transducer 1364 (in an ultrasonic device 1304). Instead, the generator 102 may be electrically coupled to a load having predetermined characteristics (e.g., a predetermined impedance, predetermined reactive properties, etc.) The generator 102 may sense the change in the load to determine that the charge is complete.

If the charge is not complete, the generator 102 may continue to provide the charge signal at 1506. If the charge is complete, the generator 102 may provide the therapeutic drive signal at 1510. In some embodiments, instead of providing the therapeutic drive signal at 1510, the generator 102 may enter a state where it is configured to provide the therapeutic drive signal in response to actuation of the actuation switch 1324. The generator 102 may determine whether the charge is complete in any suitable manner. For example, in some embodiments, the status of the device may indicate a length in time that the charge signal is to be provided. For example, the status of the device may indicate that a charge signal is to be provided for a defined amount of time (e.g., one minute) when the device is initially connected to the generator 102 and then for a second defined amount of time (e.g., 20 seconds) after each firing of the device. Also, in some embodiments, the generator 102 may be directly or indirectly in communication with the charge management circuit 1316 to monitor a charge status of the energy storage device 1314. In some embodiments, the generator 102 is configured to determine the charge status of the energy storage device 1314 based on characteristics of the charge signal. For example, a current and voltage level of the charge signal may provide the generator 102 with an indication of the voltage drop and, therefore, the charge status of the energy storage device 1314.

Figure 16:
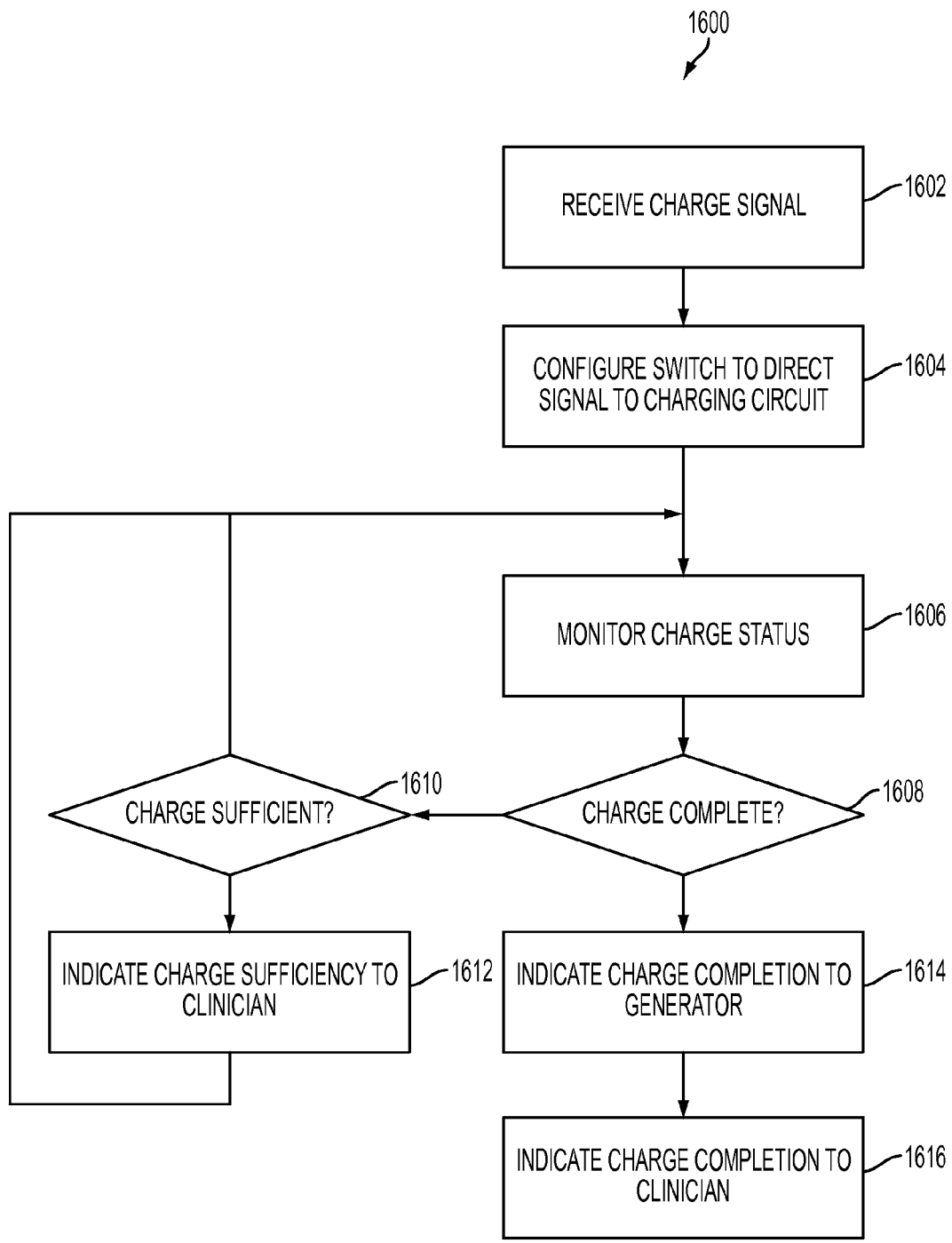
FIG. 16 is a flow chart illustrating one embodiment of a process flow that may be implemented by a surgical device, such as one of the devices, to charge an energy storage device.

FIG. 16 is a flow chart illustrating one embodiment of a process flow 1600 that may be implemented by a surgical device, such as one of the devices 1304, 1306, to charge an energy storage device 1314. At 1602, the device may receive a charge signal. At 1604, the device may configure the switch 1310 to direct the charge signal to the energy storage device 1314 (e.g., via the rectifier 1312 and, in some embodiments, the charge management circuit 1316. In some embodiments, the device may configure the switch 1310 before the charge signal begins. For example, before the charge signal is received, the device may configure the switch 1310 to electrically connect the generator 102 to the energy storage device 1314 and/or place the switch in a third state where the generator 102 is not in electrical communication with either the electrodes 1322 (in an electrosurgical device 1306) or the transducer 1364 (in an ultrasonic device 1304), for example as described above with respect to action 1508.

At 1606, the device may monitor the charge status of the energy storage device 1314. For example, the charge management circuit 1316 may monitor the charge on the energy storage device 1314. This may be accomplished in any suitable manner. For example, when the energy storage device 1314 comprises one or more capacitors and/or batteries of certain chemistries, the charge management circuit 1316 may monitor the voltage drop across the capacitors. When the energy storage device 1314 comprises Li-ion batteries or batteries of similar chemistries, the charge management circuit (e.g., the charge monitoring circuit 1360) may monitor charge provided to and expended from the battery, sometimes referred to as coulomb counting.

At 1608, the device (e.g., the charge management circuit 1316) may determine whether the energy storage device 1314 is completely charged. For example, this may be determined when the energy storage device 1314 exhibits a voltage drop above a given threshold, has received a net increase of a threshold amount of charge, etc. If the charge is complete, the device may indicate completion of the charge to the generator 102 at 1614. For example, the charge management circuit 1316 may be configured to generate an indication signal as indicated above. Also, in some embodiments, to the charge management circuit 1316 may indicate completion of the charge to the generator 102 by modifying a state of the switch 1310, for example, to a third state where the generator 102 is not electrically coupled to either the energy storage 1314 or the electrodes 1322 (in an electrosurgical device 1306) or the transducer 1364 (in an ultrasonic device 1304). In some embodiments, the device also indicates completion of the charge to the clinician using the device at 1616. For example, the charge management circuit 1316 may provide a charge completion signal to the display 1328, haptic feedback device 1329, etc. The display 1328, haptic feedback device 1329, etc., in turn, may indicate charge completion to the clinician in any suitable manner.

If the charge is not complete at 1608, the device may continue to monitor the charge status of the energy storage device 1314 at 1606. Optionally, when the charge is not complete at 1608, the device (e.g., the charge management circuit 1316) may determine whether the charge level of the energy storage device 1314 is sufficient for one firing of the device. For example, the charge may be considered sufficient for one firing of the device when a voltage, net charge provided to the device 1314, or other suitable measure has reached a second threshold. The second threshold may correspond to a level of charge that is less than a complete charge. If the level of charge is sufficient for a single firing, the device (e.g., the charge management circuit 1316) may indicate this status to the clinician at 1612. For example, the indication may be displayed to the clinician via the display 1328.

It will be appreciated that FIGS. 15 and 16 illustrate just one example manner in which the generator 102 may operate to charge the energy storage device 1314. In some embodiments, the generator 102 may not be configured to discriminate between devices that are and are not enabled to harvest signal energy. For example, the generator 102 may simply be configured to provide a therapeutic drive signal when requested by the device. In these embodiments, the device may utilize the therapeutic drive signal both for driving the electrodes 1322 (in an electrosurgical device 1306) or the transducer 1364 (in an ultrasonic device 1304) and for charging the energy storage device 1314. For example, the charge management circuit 1316 or other suitable component of the device may be configured to request the therapeutic drive signal when it is desirable to charge the charge monitoring device. For example, the device may provide the generator 102 with a signal similar or identical to the signal generated by the actuation switch. At these times, the switch 1310 may be configured to direct the therapeutic drive signal to the energy storage device 1314, where it may be used for charging. As described above, in some embodiments, an electrosurgical drive signal may be more desirable for charging the energy storage device 1314, even in an ultrasonic instrument such as 104, 1304. Accordingly, the surgical device may be configured to request an electrosurgical drive signal for charging the energy storage device 1314.

Figure 17:
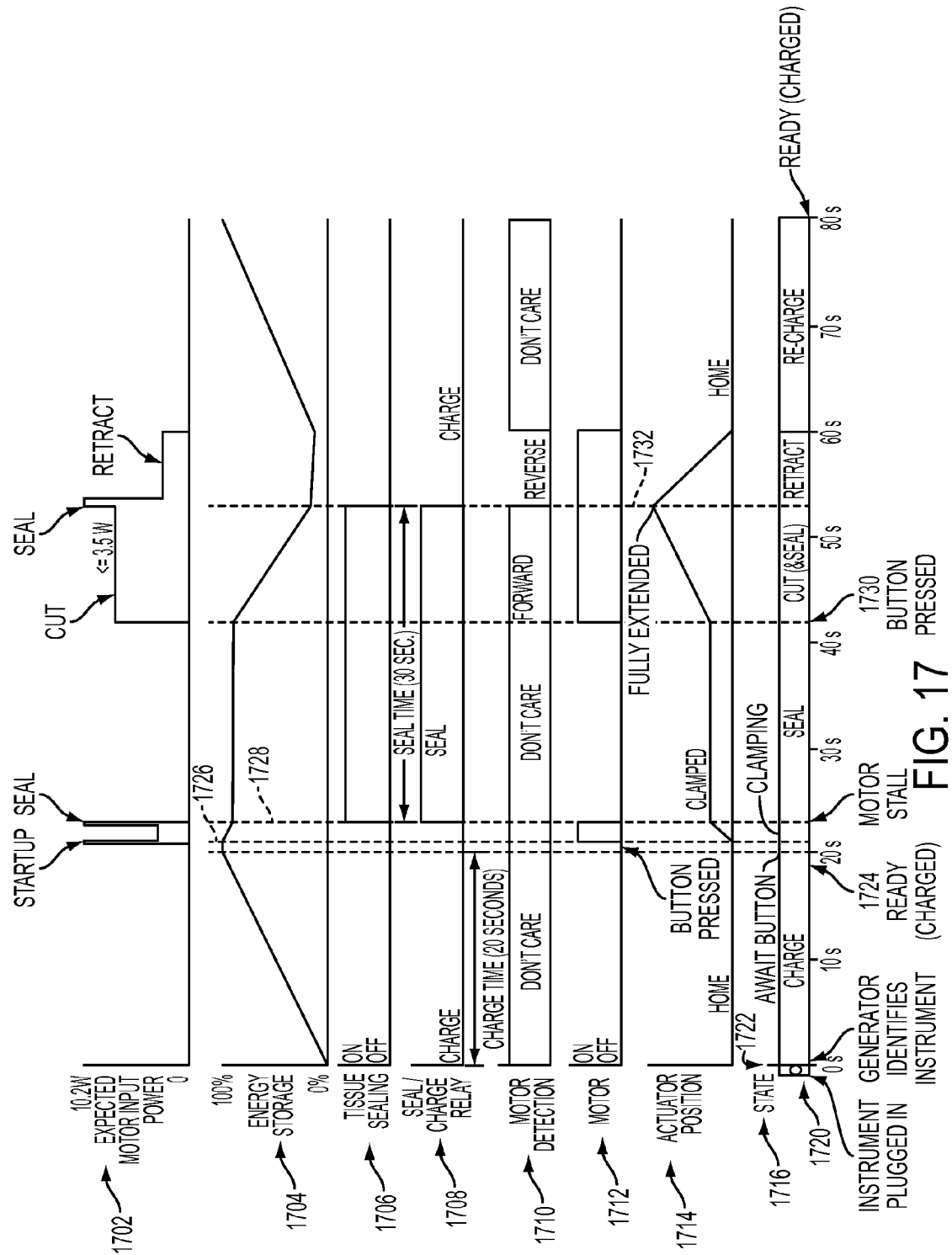
FIG. 17 is a timing diagram illustrating one embodiment of a charging and firing cycle of the electrosurgical device.

FIG. 17 is a timing diagram illustrating one embodiment of a charging and firing cycle of the electrosurgical device 1306. It will be appreciated that a similar cycle may be utilized with an ultrasonic instrument 1304. Also, it will be appreciated that the timing diagram of FIG. 17 may apply to embodiments utilizing an energy storage device 1314 comprising a battery, such as a Li-ion battery, as well as to embodiments utilizing an energy storage device comprising one or more capacitors. Row 1702 indicates the output of the motor 1334 in watts. Row 1704 indicates the charge level of the energy storage device 1314. Row 1706 indicates the status of the electrodes 1322 (e.g., whether they are providing a therapeutic signal to the tissue). Row 1708 indicates the position of the switch 1310. Row 1710 indicates the direction of the motor 1334. Row 1712 indicates the state of the motor (e.g., on or off). Row 1714 indicates the position of the translating member (such as the translating member 173). Row 1716 shows the state of the surgical system 1300.

At 1720, the instrument 1300 may be connected to or plugged-in to the generator 102. At this point, the generator 102 may identify the instrument, for example, as described herein at 1502 and 1504. The instrument may be identified at 1722. After the instrument is identified, the energy storage 1314 may begin to charge. For example, the switch 1310 may be set to a charge setting where the generator 102 is coupled to the energy storage, as described herein. The charge status of the energy storage 1314 may rise after 1722, as indicated in row 1704. At 1724, the energy storage 1314 may be fully charged (and/or sufficiently charged for a single firing of the device 1306). As illustrated, the time between the beginning of the charge signal and the full charging of the energy storage 1314 may be about twenty (20) seconds, though; different implementations may have different values.

At 1726, the clinician may trigger an actuation switch 1324 indicating that a cutting and sealing operation is to begin. This may transition the device 1306 to a clamp mode. The motor controller 1330 may cause the motor 1334 to engage the jaw/blade mechanism 1342 (e.g., by advancing the translating member 173 distally). Referring to row 1702, the motor may initially draw peak power, enter a period of constant power while the mechanism 1342 is engaged and then again draw peak power as the jaw members 167, 169 clamp tissue there between. When the clamping is complete, at 1728, the switch 1310 may be transitioned to connect the generator 102 to the electrodes 1322 and the generator may begin to provide a therapeutic drive signal, indicated in columns 1708 and 1706, respectively. It will be appreciated that the switch 1310 may be transitioned at any time after the completion of the charging at 1724. At 1730, the clinician may actuate an actuation switch 1324 indicating that cutting is to be completed. (In some embodiments, the device 1306 will automatically determine when cutting is to be completed, for example, based on the amount of time that the therapeutic drive signal has been applied to the electrodes 1322, the state of the tissue as measured by a sensor 1332, etc.). At 1730, the motor 1334 is again engaged in a forward direction to further actuate the jaw/blade mechanism 1342. Columns 1702 and 1704 illustrate the resulting effects on the charge state of the energy storage device 1314 and the power drawn by the motor 1334. When the jaw/blade mechanism is fully extended at 1732 (shown in column 1714), the motor 1334 may again draw peak current (column 1702). Full extension of the jaw/blade mechanism may be indicated, for example, by an end of stroke sensor 1338. As the cutting and sealing operation is then complete, the motor controller 1330 may reverse the direction of the motor 1334 (indicated at 1710 and 1702) to return the jaw/blade mechanism 1342 to its un-actuated state. At this point, the switch 1310 may be again configured for charging. The generator 102 may provide a charge signal and the energy storage device 1314 may begin to re-charge, as shown in column 1704.

The energy harvesting circuit 1302 may be configured to meet different power parameters for different implementations. For example, in some embodiments of an electrosurgical device 1306 where the energy harvesting circuit 1302 is to power a drivetrain for actuating the jaw/blade mechanism 1342, the energy harvesting circuit may be configured to provide 3.5 watts (W) at 15 volts (V) continuously and 10.5 W peak power during start-up and stall conditions of the motor 1334 (e.g., 0.7 amperes (A) at 15 V). In other embodiments for powering a drivetrain for a jaw/blade mechanism 1342, the energy harvesting circuit may be configured to provide 50 W over the course of a firing cycle which may take, for example six seconds. Charging specifications may be determined based on specific use requirements. In some embodiments, for example, it may be desirable for the energy storage device 1314 to take an initial charge in about one minute or less and to "re-charge" after discharge in about twenty seconds or less. Of course, different embodiments and different surgical situations may utilize devices with different parameters.

The energy storage device 1314 may comprise any suitable device or component capable of storing electrical energy. As indicated above, in some embodiments, the energy storage device 1314 comprises one or more super capacitors or other suitable capacitors such as high voltage electrolytic capacitors. Equation (1) below indicates the energy that may be stored in a capacitor:

$$E_C(C,V)=1/2CV^2 \qquad (1)$$

A capacitor or bank of capacitors may be selected to provide the desired amount of energy (in some example embodiments, 150 J or more). In some embodiments, it is difficult to completely discharge a capacitor. Accordingly, the capacitor or bank of capacitors may be selected with an energy storage potential that is higher than what is actually desired. For example, when a capacitor is discharged to 50% of its initial voltage, it expends 75% of its initial stored energy. Accordingly, it may be desirable to select a capacitor or capacitors with an energy capacity at least 133% of the total energy to be delivered and discharge the capacitors to 50% of their initial voltage.

Also, as indicated above, the energy storage device 1314 may comprise one or more batteries, such as Li-ion batteries. In some embodiments, it may be desirable to select fast-charging Li-ion batteries such as, for example, the MOLICEL IBR18650BC available from E-ONE MOLI ENERGY. Also, various embodiments may utilize lithium ion capacitors, such as those available from TAIYO YUDEN.

Figure 18:
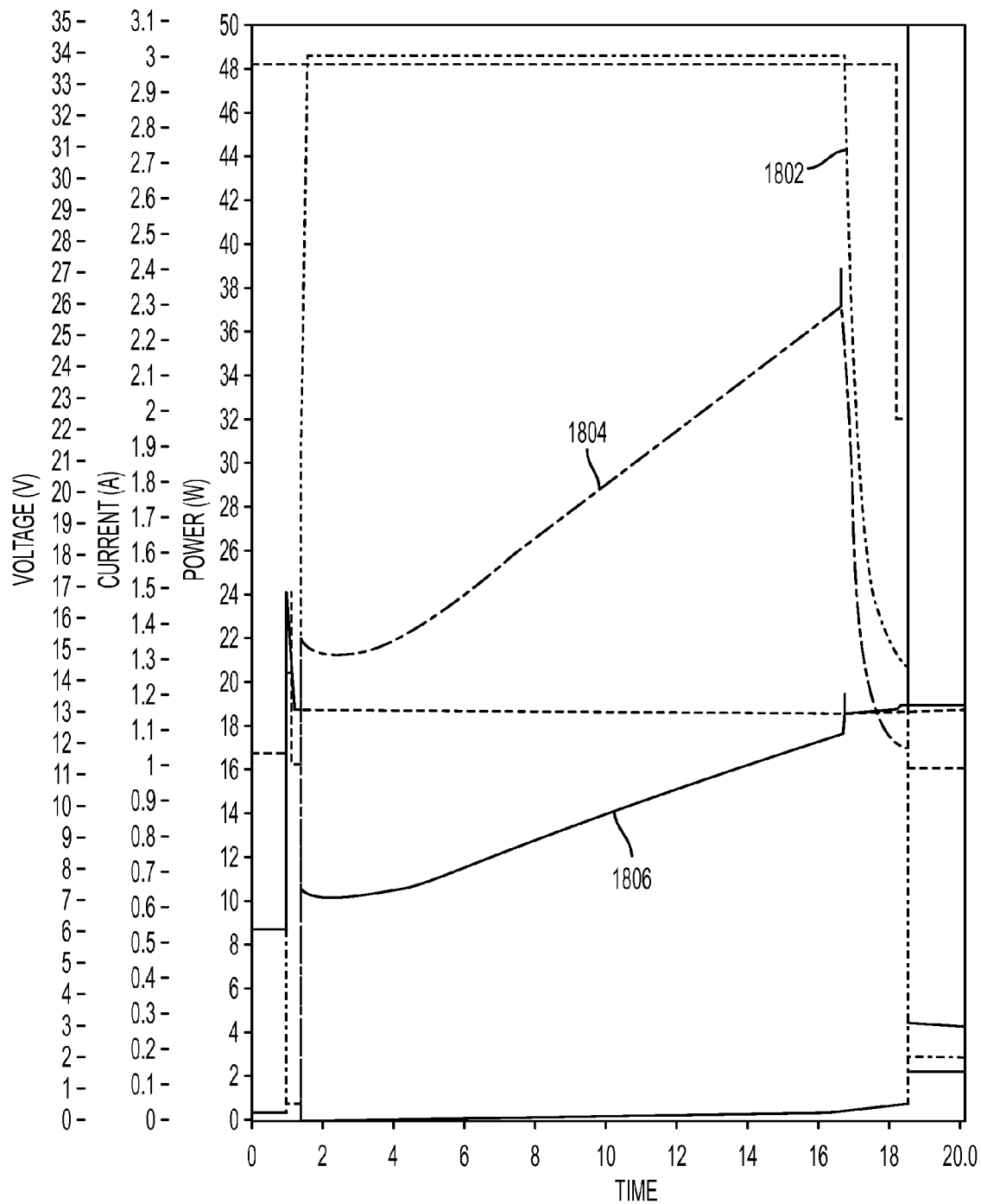
FIG. 18 is a graph illustrating a charging cycle of one embodiment of an energy storage device comprising a bank of super capacitors exhibiting a collective capacitance of 5 farads (F).

Different types of suitable energy storage devices 1314 may exhibit different charge and discharge characteristics. For example, in some embodiments, the energy storage device 1314 may comprise one or a bank of super capacitors. For example, FIG. 18 is a graph illustrating a charging cycle of one embodiment of an energy storage device 1314 comprising a bank of super capacitors exhibiting a collective capacitance of 5 farads (F). In FIG. 18, plot 1802 corresponds to the current provided to the energy storage device 1314, plot 1804 corresponds to the power provided to the energy storage device 1314 and plot 1806 corresponds to the voltage drop across the energy storage device 1314. As illustrated, the energy storage device 1314 was charged from a completely discharged state to a full charge of about 13 V in about 17 seconds (s). It was found that, when starting from an initial energy storage device 1314 voltage of about 4 V, rather than a completely discharged state, the energy storage device 1314 reached its full charge in about 12.5 s. On discharge, with the output configured to 15 V and an example 20 ohm (Ω) resistive load (750 mA, 11.25 W), the energy storage device 1314 delivered between about 180 and about 195 J, with an average of 188 J.

As indicated above, some embodiments of the energy storage device 1314 may also comprise batteries, such as a Li-ion battery. In one example utilizing a Li-ion battery model number UR18650RX available from PANASONIC, the battery was discharged to a voltage level of 2.9 V, which is below the rated Li-ion lockout voltage (3.22 V) and below the fast charge threshold (3.1 V). This was to approximate a charge from a fully discharged state. For some embodiments, the generator 102 may be configured to provide a charge signal of 5 A to the energy storage device 1314 to charge the Li-ion battery. From this state, the energy storage device 1314 required approximately one minute to reach full charge. After charging, the energy storage device 1314 was able to deliver about 350 J to a load from a 12 V supply output. After delivering the load current, the voltage of the energy storage device 1314 dropped below its lockout voltage (e.g., 3.22 V).

Figure 19:
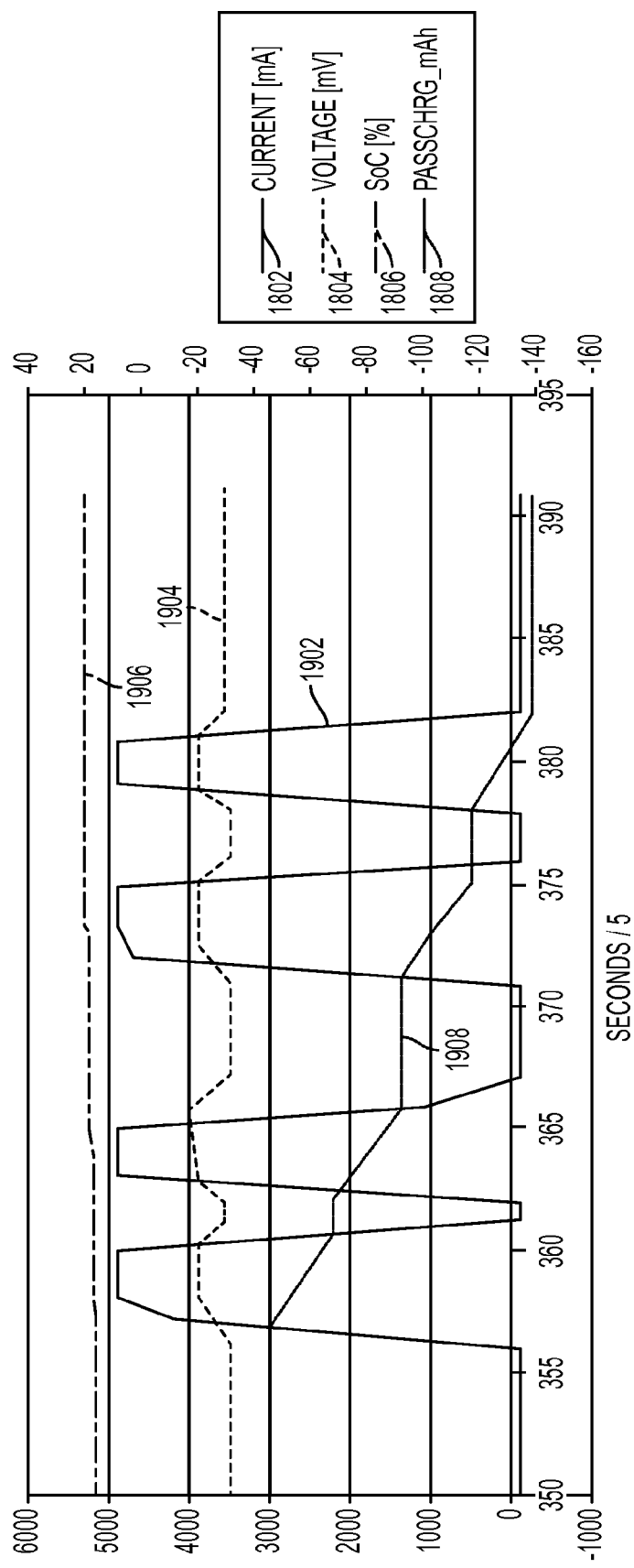
FIG. 19 is a graph illustrating an example Li-ion battery energy storage device placed through four consecutive charge and discharge cycles.

In implementations where less than a threshold amount of energy (e.g., 150 J) is delivered from the battery, re-charge times may be less. For example, the Li-ion battery energy storage device 1314 described was placed through four consecutive charge cycles. FIG. 19 is a graph illustrating an example Li-ion battery energy storage device (e.g., as described above) placed through four consecutive charge and discharge cycles. In FIG. 19, the current provided to the battery is indicated by 1902; the voltage drop across the battery is indicated by 1904, the state of charge of the battery (by percentage or %) is indicated by 1906 and the passed charge, measured in miliampere-hours (mAh) is indicated by 1908. As shown, the energy storage device 1314 was at about a 16% state of charge when the cycle began. The illustrated four cycle charge raised the state of charge from 16% to 21% and the passed charge from 45 mAh to 141 mAh, respectively. It was found that each of the four charge cycles provided approximately 300 J of energy to the energy storage device 1314.

In various embodiments, the generator 102 may provide a combined drive signal that simultaneously comprises a charge signal portion and a therapeutic drive signal portion. For example, the energy harvesting circuit may be configured to separate the charge signal portion and therapeutic signal portions, directing the charge signal portion to the energy storage device 1314 the therapeutic drive signal portion to the electrodes 1322 (or transducer 1364 in the case of an ultrasonic device 1304). The combined drive signal may be provided in any suitable manner. For example, in some embodiments, the charge signal portion and the therapeutic signal portion may be present in the combined drive signal at different frequencies. For example, the therapeutic drive signal portion may be present at relatively high frequencies while the charge signal portion may be present at relatively low frequencies including, for example, at direct current or DC. Also, in some embodiments, the charge signal portion and therapeutic drive signal portion may be present in the combined drive signal in different phases. For example, the therapeutic drive signal portion may be present on the positive phase of the combined signal while the charge signal portion may be present on the negative phase of the combined signal.

Figure 20:
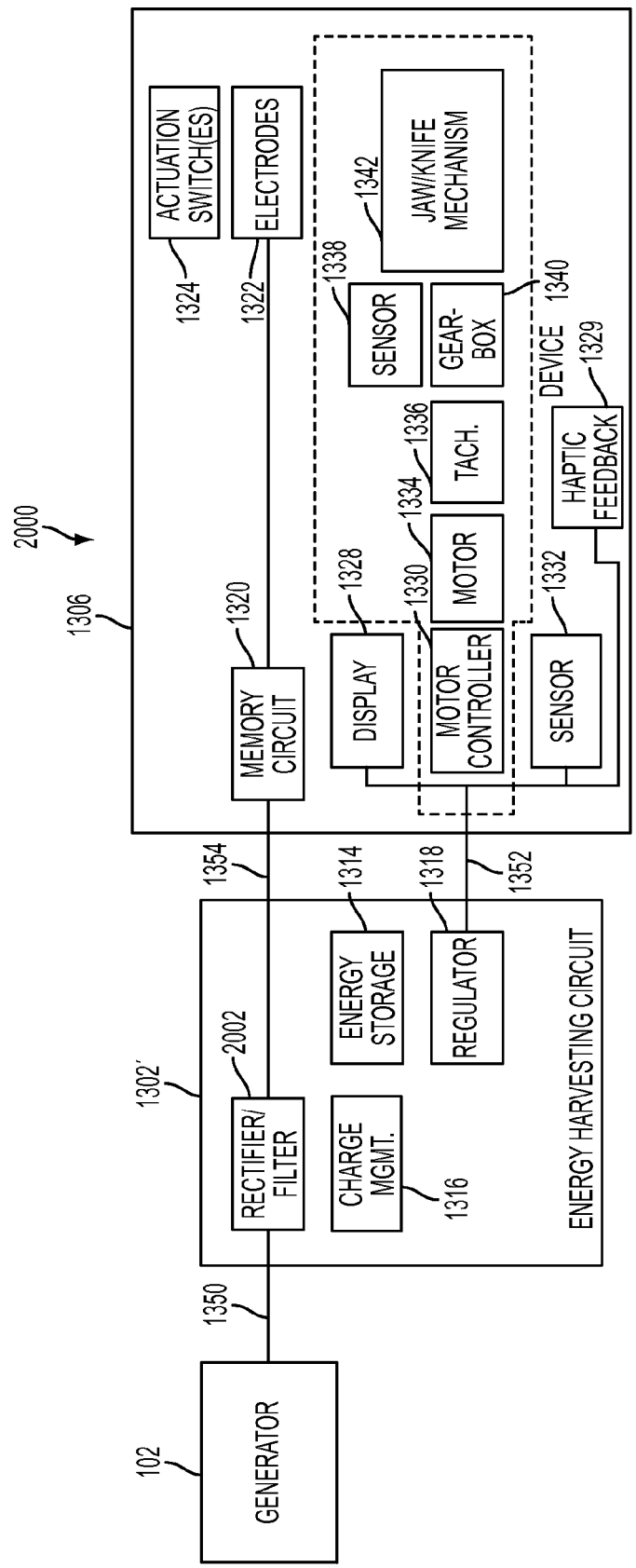
FIG. 20 is a block diagram illustrating one embodiment of a surgical system configured for harvesting energy provided by a generator as a combined drive signal.

FIG. 20 is a block diagram illustrating one embodiment of a surgical system 2000 configured for harvesting energy provided by a generator as a combined drive signal. The system 2000 comprises a modified energy harvesting circuit 1302'. In lieu of the switch 1310, the energy harvesting circuit 1302' comprises a signal separator circuit 2002 that may include a rectifier and/or a filter. The signal separator circuit 2002 may be configured to separate the combined drive signal into the therapeutic drive signal portion, which may be directed to the electrodes 1322 and the charge signal portion, which may be directed to the energy storage device 1314 for charging. The signal separator circuit 2002 may utilize any suitable hardware and/or software. For example, in embodiments where the combined signal is split by frequency, the signal separator circuit 2002 may comprise one or more filters. For example, a low pass filter may be applied, with the output (constituting the charge signal portion) provided to the energy storage 1314. A high-pass filter may also be applied, with the output (constituting the therapeutic signal portion) being applied to the electrodes 1322. Various other filtering and/or rectification may also be applied as the implementation warrants. Also, for example, in embodiments where the combined signal is split by polarity, the signal separator circuit 2002 may comprise one or more rectifiers configured to provide the positive polarity portion of the combined signal (e.g., the therapeutic drive signal portion) to the electrodes 1322 and the negative polarity portion of the combined signal (e.g., the charge signal portion) to the energy storage 1314. It will be appreciated that the polarities of the respective signal portions may also be reversed.

Figure 21:
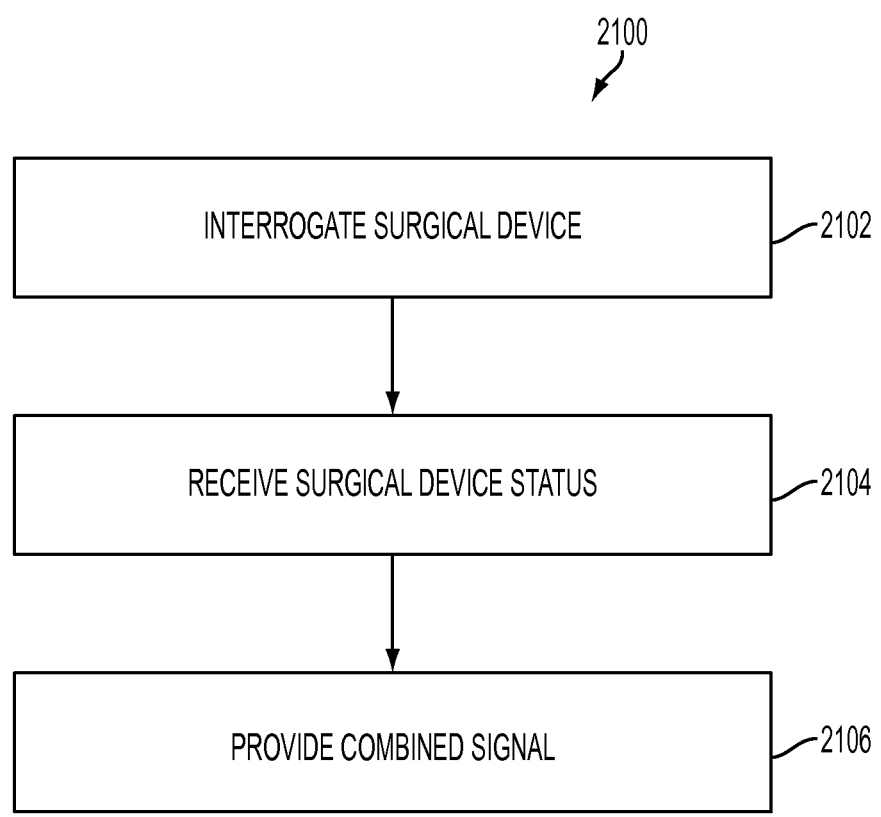
FIG. 21 is a flow chart illustrating one embodiment of a process flow that may be executed by the generator in the surgical system of FIG. 20.

FIG. 21 is a flow chart illustrating one embodiment of a process flow 2100 that may be executed by the generator 102 in the surgical system 2000 of FIG. 20. At 2102, the generator may interrogate the surgical device (which may be an ultrasonic surgical device like 1304, an electrosurgical device like 1306, or other suitable device). The generator 102 may receive the status of the surgical device at 2104. Actions 2102 and 2104 may be similar to actions 1502 and 1504 described herein above. At 2106, the generator 102 may provide the combined signal to the device.

Figure 22:
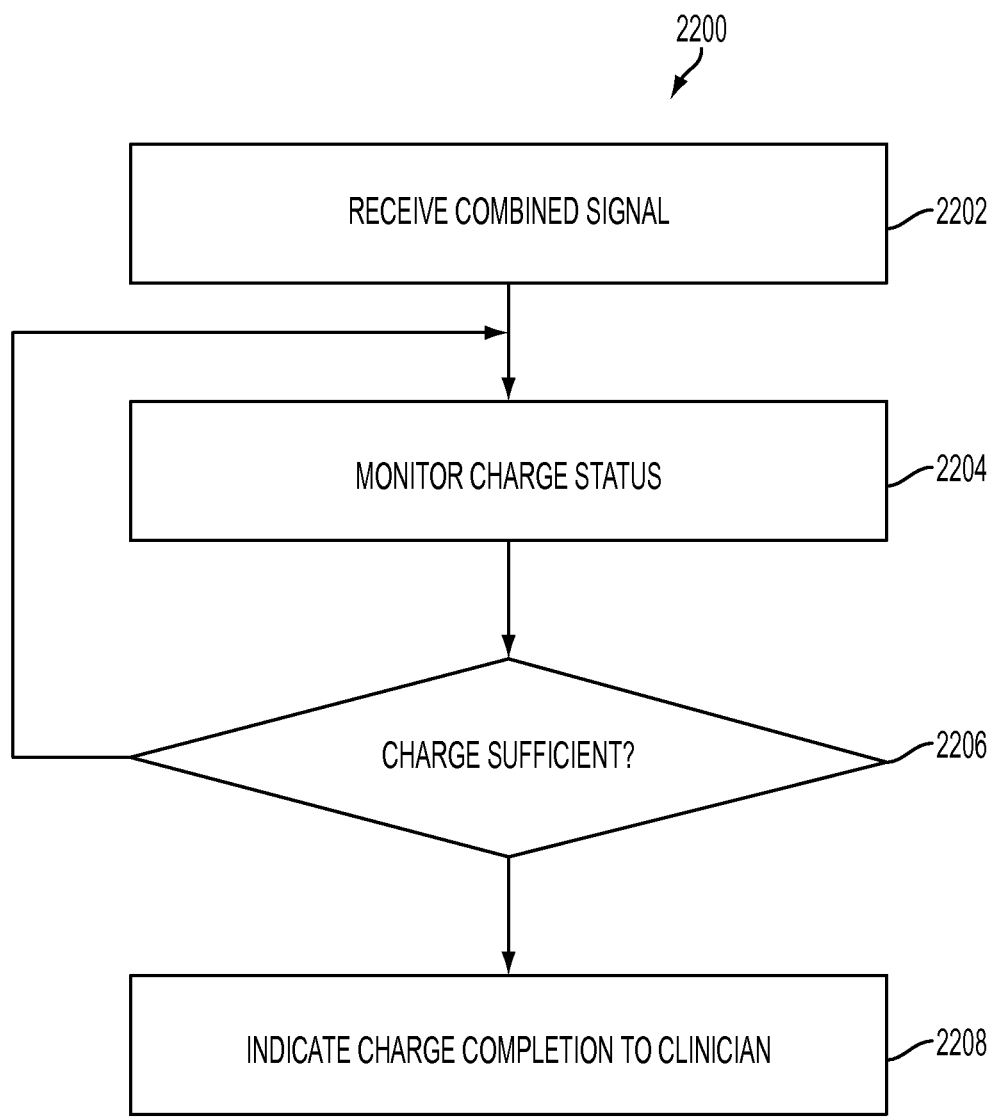
FIG. 22 is a flow chart illustrating one embodiment of a process flow that may be executed by a surgical device to harvest energy from the generator in the surgical system of FIG. 20.

FIG. 22 is a flow chart illustrating one embodiment of a process flow 2200 that may be executed by a surgical device to harvest energy from the generator 102 in the surgical system 2000 of FIG. 20. The process flow 2200 may be executed by any suitable surgical device capable of energy harvesting including, for example, the ultrasonic surgical device 1304, the electrosurgical device like 1306, etc. At 2202, the device may receive the combined drive signal. As shown, because the combined drive signal comprises both the therapeutic drive signal portion and the charge signal portion, it may not be necessary for the device to alternately direct the combined drive signal to the energy storage device 1314 and the electrodes 1322. The device may monitor the charge status of the energy storage device 1314 at 2204. If the charge is sufficient at 2206, the device may indicate completion of the charge to the clinician at 2208. For example, 2204, 2206 and 2208 may be similar to actions 1606, 1608, and 1614 described herein above. In some embodiments, the device may also indicate when the charge level of the energy storage device 1314 is sufficient for a single firing of the device, as described above with respect to 1610 and 1612. In some example embodiments, the device may additional indicate to the generator 102 that the charge is complete. In response, the generator 102 may modify the combined drive signal so as to omit the drive signal portion. Similarly, in some embodiments, the generator 102 may be in communication with the device and may modify the combined drive signal to include the therapeutic drive signal portion only when requested by the device or clinician, for example, as illustrated in FIG. 17.

Figure 23:
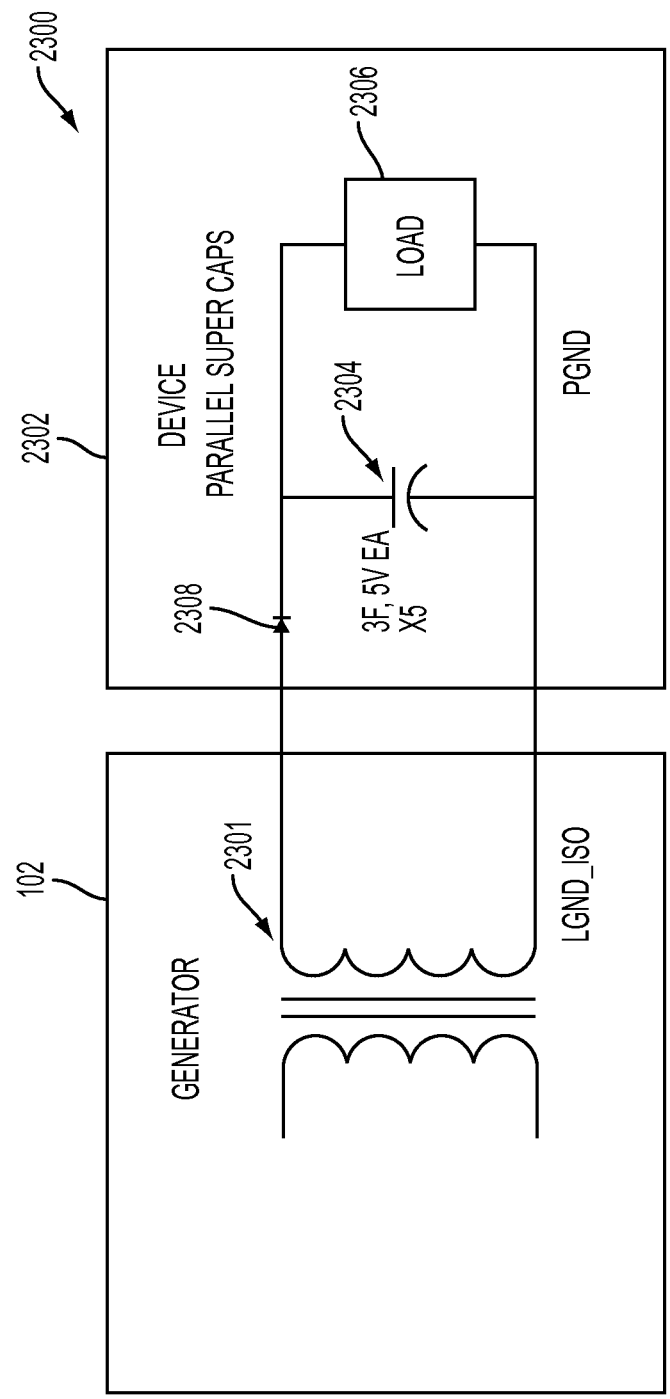
FIG. 23 is a diagram of one embodiment of a surgical system utilizing super capacitors as energy storage devices.

Various embodiments of the surgical systems described herein utilize an energy storage circuit comprising one or more capacitors. FIG. 23 is a diagram of one embodiment of a surgical system 2300 utilizing capacitors in an energy storage device. In FIG. 23, the generator 102 utilizes a transformer or other suitable component to isolate itself from the device 2302 (and, therefore, the patient). The system 2300 comprises a bank 2304 of five (5) 3 Farad (F) capacitors in parallel with one another and with the load 2306 to be powered. Examples of such capacitors are the model number PAS1016LS2R5205 capacitors available from TAIYI YUDEN. The load, for example, may comprise the display 1328, the drive train 1326, the sensor 1332, the haptic feedback device 1329, or any other suitable component of the device 2302. A half-wave rectifier 2308 may rectify the charge signal so as to charge the capacitors 2304.

Figure 24:
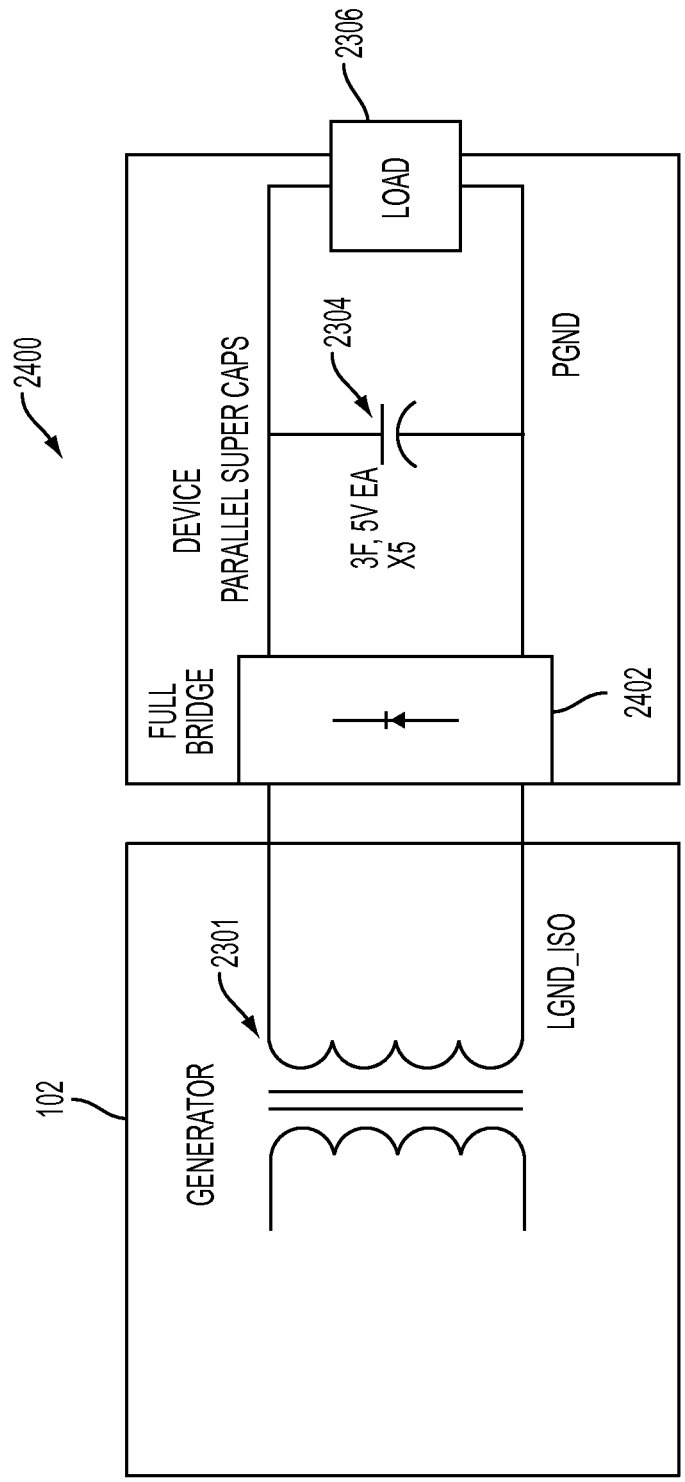
FIG. 24 is a diagram of another embodiment of a surgical system utilizing capacitors in an energy storage device.

FIG. 24 is a diagram of another embodiment of a surgical system 2400 utilizing capacitors in an energy storage device. The system 2400 may be similar to the system 2300, but the half-wave rectifier 2308 may be replaced with a full wave rectifier 2402.

Figure 25:
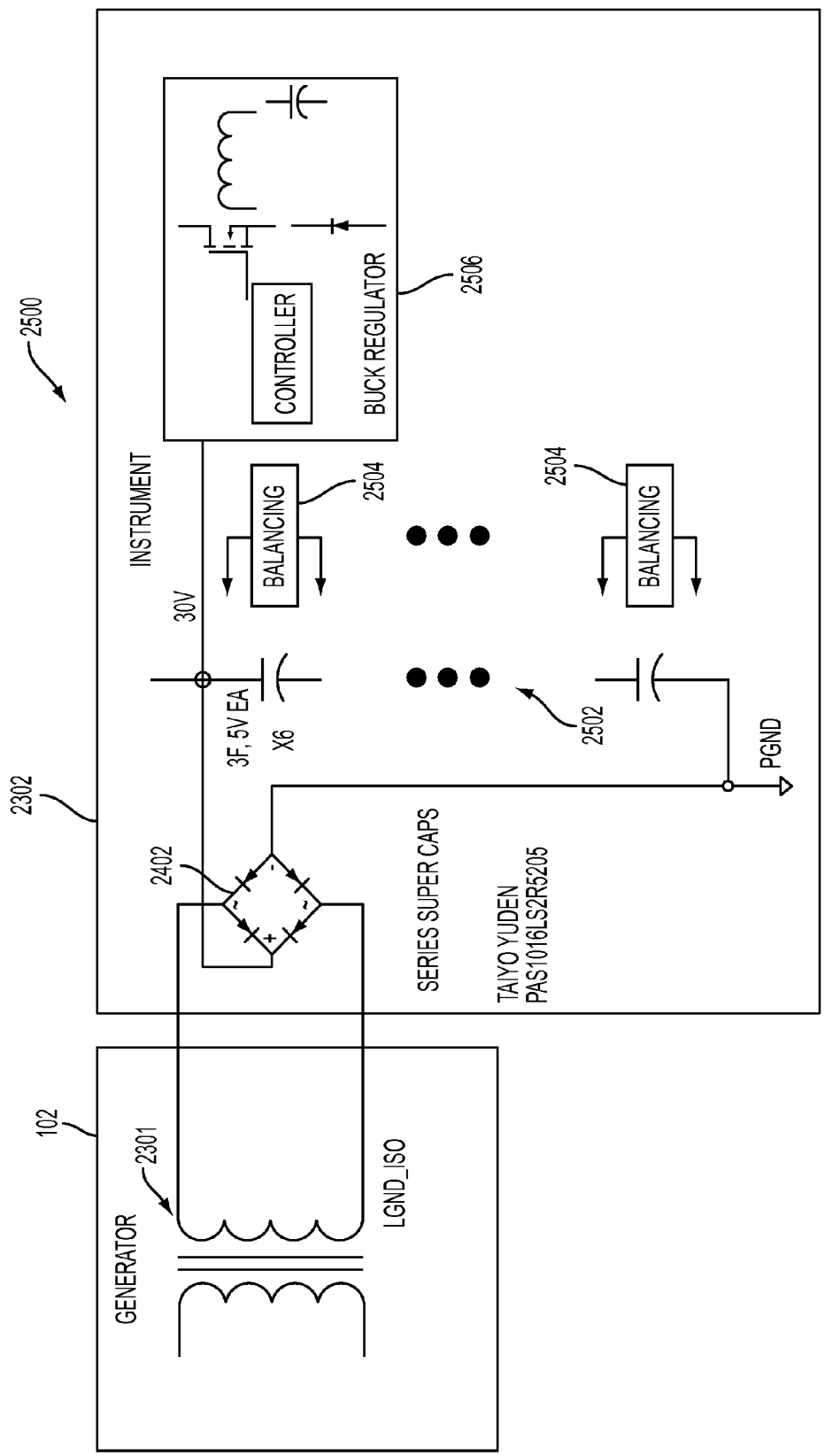
FIG. 25 is a diagram of one embodiment of a surgical system utilizing series capacitors in an energy storage device.
Figure 26:
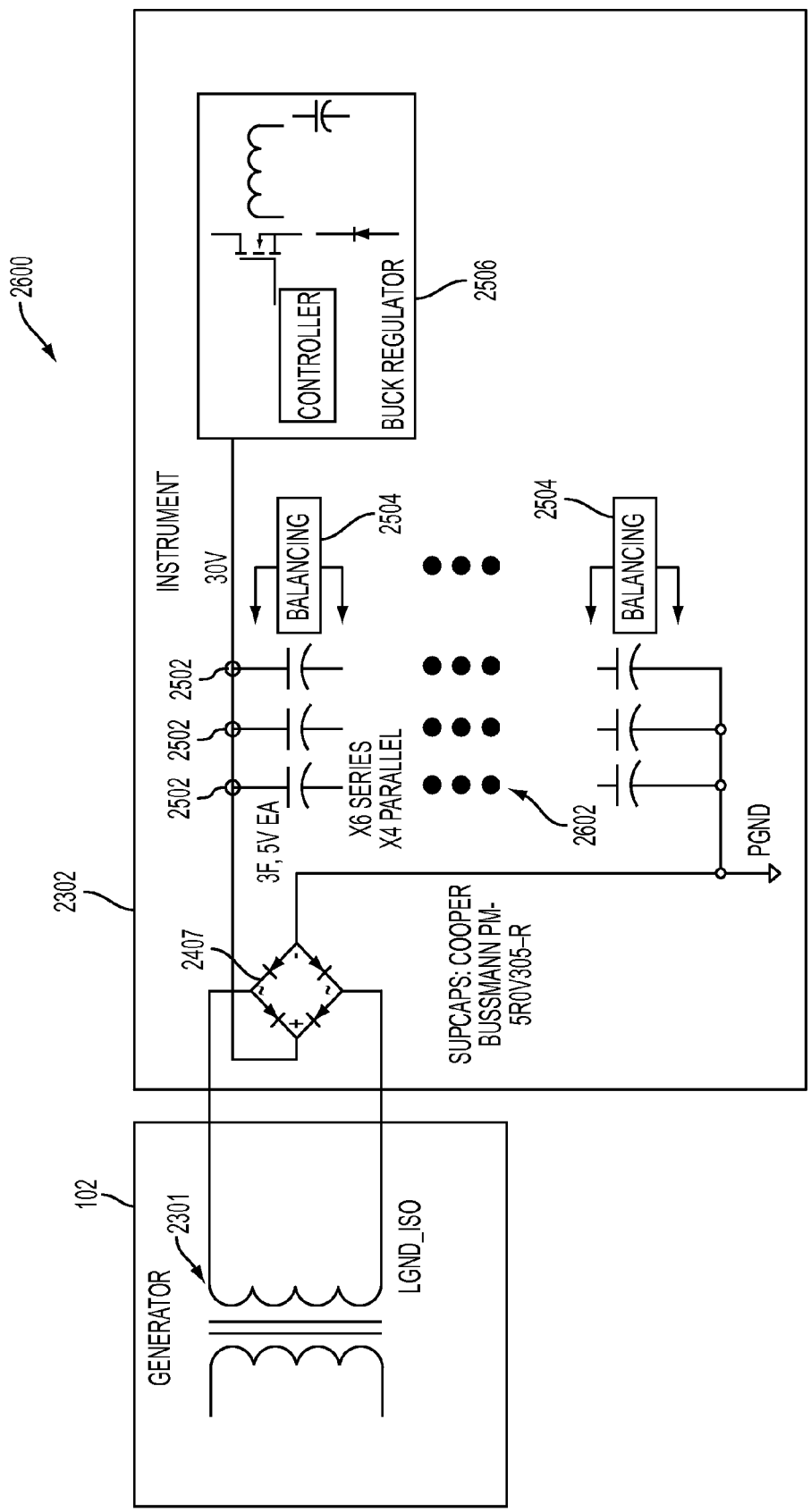
FIG. 26 is a diagram of one embodiment of a surgical system utilizing an alternative capacitor bank as an energy storage device.

FIG. 25 is a diagram of one embodiment of a surgical system 2500 utilizing series capacitors in an energy storage device. In FIG. 25, the parallel capacitor configuration of the systems 2300 and 2400 is replaced with a bank of series connected capacitors 2502. The bank 2502 may comprise six capacitors rated at 3 F and 5V. Additionally, the device 2302 may comprise one or more balancing circuits 2504 shunting the capacitors of the bank 2502 so as to prevent overvoltage conditions in individual capacitors on charging and discharge. The output of the capacitor bank 2502 may be provided to a regulator 2506. The regulator 2506 is illustrated as a buck regulator, though any sort of linear and/or switched regulator may be used. FIG. 26 is a diagram of one embodiment of a surgical system 2600 utilizing an alternative capacitor bank as an energy storage device. For example, the system 2600 may utilize a capacitor bank comprising four examples of the capacitor bank 2502 connected in parallel.

Figure 27:
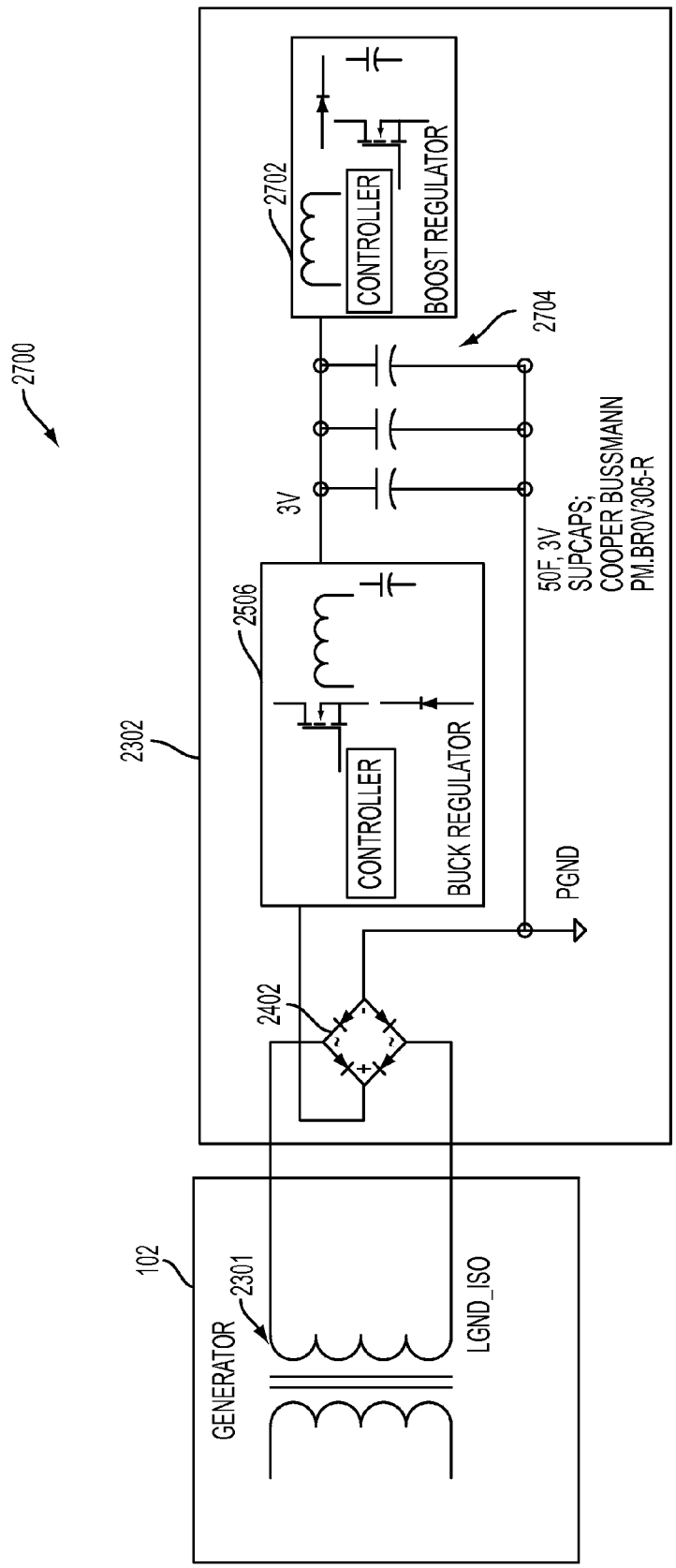
FIG. 27 is diagram of one embodiment of a surgical system utilizing multiple regulators in conjunction with a capacitor bank.

FIG. 27 is diagram of one embodiment of a surgical system 2700 utilizing multiple regulators in conjunction with a capacitor bank 2704. A buck regulator 2506 is connected between the rectifier 2402 and the capacitor bank 2704. The capacitor bank 2704 may comprise three capacitors rated at 50 F and 3V. A boost regulator 2702 is positioned between the capacitor bank 2704 and the load (not shown in FIG. 27).

Figure 28:
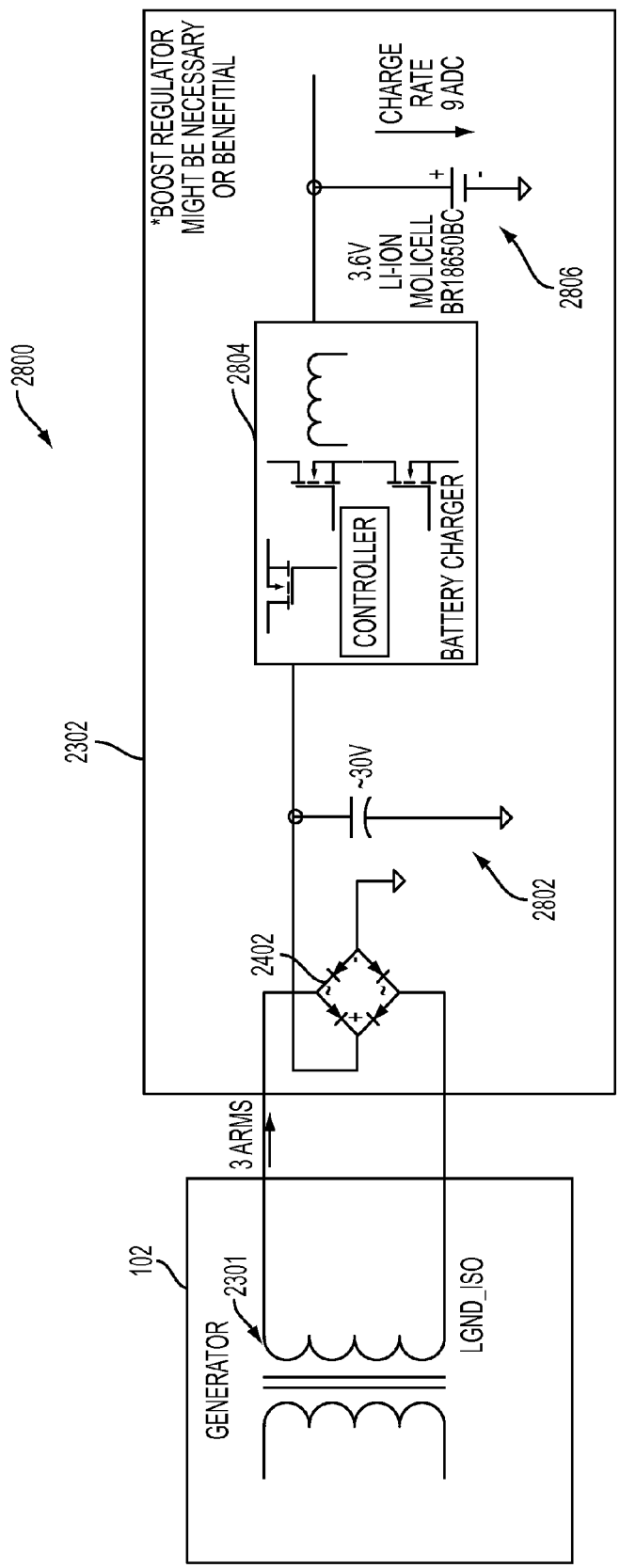
FIG. 28 is a diagram of one embodiment of a surgical system utilizing a Lithium ion battery in an energy storage device.

FIG. 28 is a diagram of one embodiment of a surgical system 2800 utilizing a Lithium ion battery 2806 in an energy storage device. The system 2800 comprises a signal smoothing capacitor 2802 in parallel with a battery charger circuit 2804 and the battery 2806. The battery charger circuit 2804 may operate in a manner similar to that described herein above with respect to the charge management circuit 1316 to manage the charging and discharging of the battery 2806. In some embodiments, a boost regulator (similar to 2702) may be positioned between the battery and the load (not shown in FIG. 28).

Figure 29:
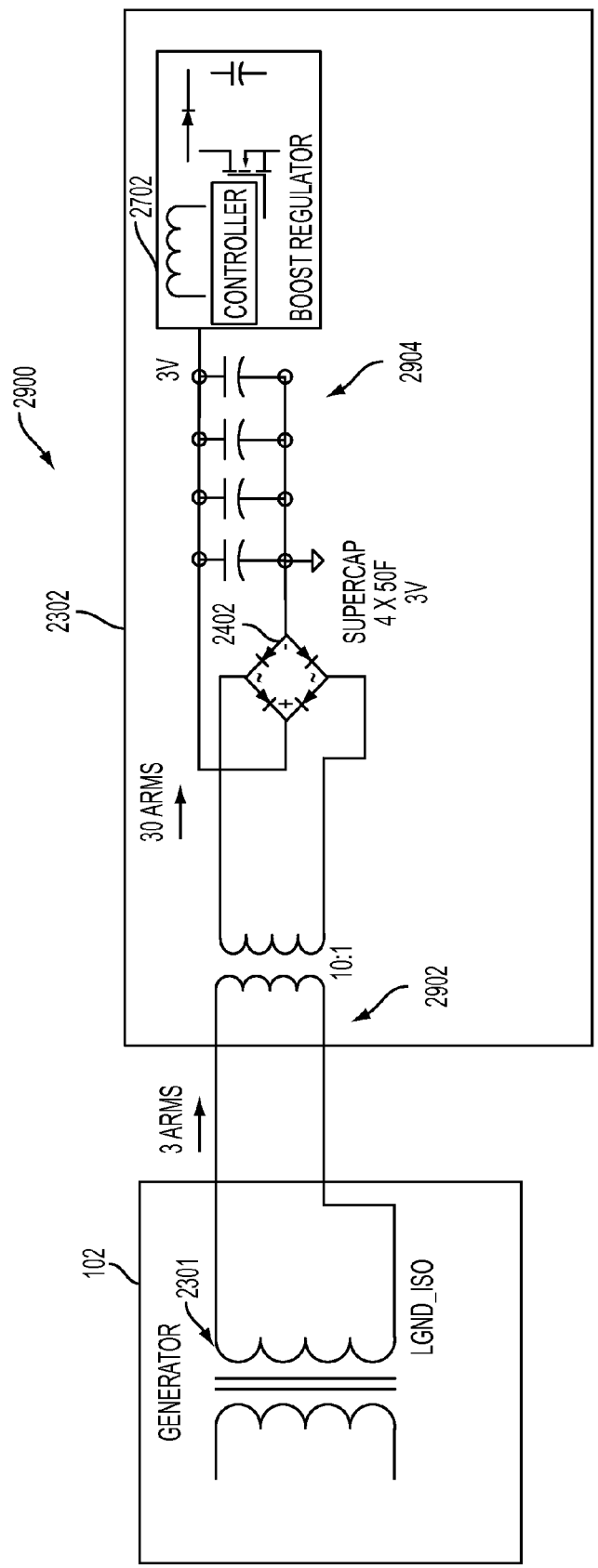
FIG. 29 is a diagram of one embodiment of a surgical system utilizing an isolated energy storage device.
Figure 30:
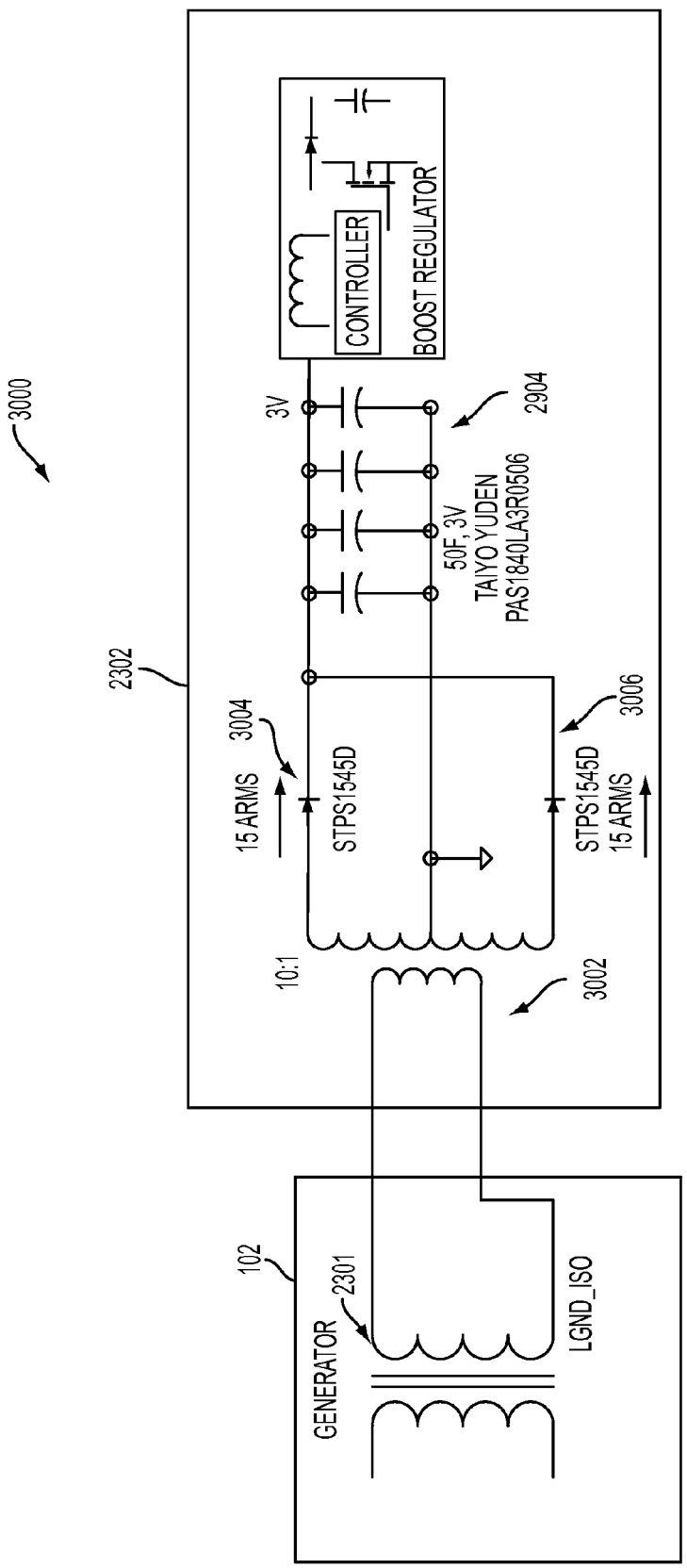
FIG. 30 is a diagram showing one embodiment of a surgical system utilizing a center-tapped isolation transformer.
Figure 31:
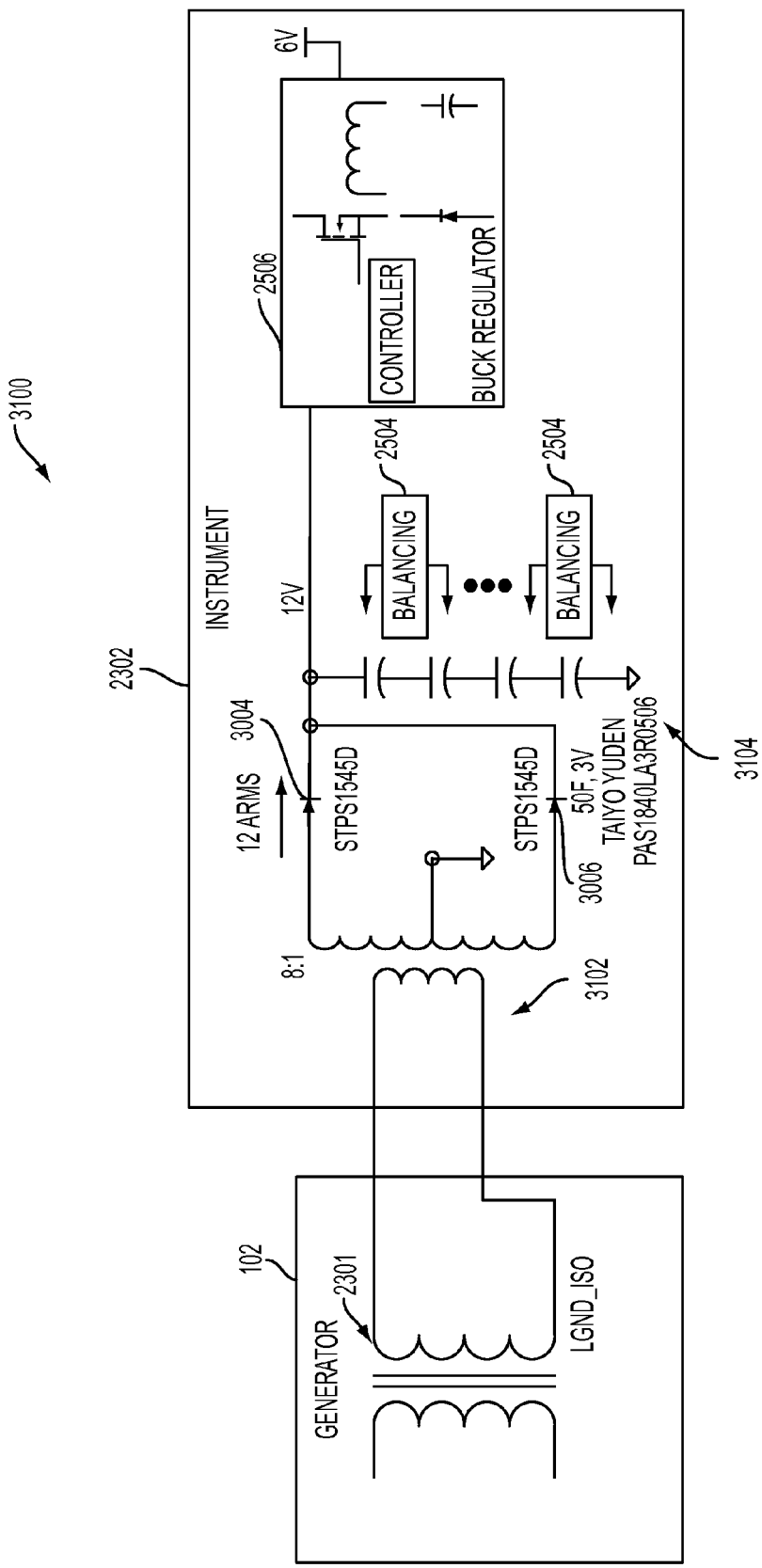
FIG. 31 is a diagram of one embodiment of a surgical system utilizing a center-tapped isolation transformer with a series-connected capacitor bank.

FIG. 29 is a diagram of one embodiment of a surgical system 2900 utilizing an isolated energy storage device. The system 2900 comprises a transformer 2902 positioned between the generator 102 and the additional components of the device 2302. The transformer 2902 may be a step-up transformer (10:1 shown in FIG. 29). This may increase the current level of the charge signal as provided to the capacitor bank 2904, allowing a larger capacitance to be charged in a given time. For example, the capacitor bank 2904 may comprise four capacitors rated at 50 F and 3V. A boost regulator 2702 may be utilized to increase the output voltage, for example, to 12 or 15 V. The transformer 2902 may also create isolation between the generator 102 and the device 2302, which may obviate the need for separate logic isolation, which may be desirable for the non-isolated embodiments described in FIGS. 23-28. FIG. 30 is a diagram showing one embodiment of a surgical system 3000 utilizing a center-tapped isolation transformer 3002. Use of the center-tapped isolation transformer 3002 may allow full-wave rectification to be performed with two diodes 3004, 3006 as opposed to the four diodes often required for a full-wave rectifier 2402. FIG. 31 is a diagram of one embodiment of a surgical system 3100 utilizing a center-tapped isolation transformer 3102 with a series-connected capacitor bank 3104. The capacitor bank 3104 may comprise four capacitors connected in series and rated at 50 F and 3 V.

Although FIGS. 23-31 show various different values and configurations for capacitors and batteries, it will be appreciated that any suitable capacitor or capacitor bank may be utilized in any of the disclosed architectures. Also, the various systems described with respect to FIGS. 23-31 may be managed by a charge management circuit, such as the circuit 1316 described herein above, that is present on device side and/or by similar functionality executed by the generator 102.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered clauses:

1. A surgical device for use with a surgical generator, the surgical device comprising: an energy storage device, the energy storage device in electrical communication with a surgical generator connection to provide energy from a surgical generator to charge the energy storage device and in electrical communication with at least one load component to be powered by the energy storage device; and an end effector; and at least one energy element for treating tissue, wherein the at least one energy element is in electrical communication with the surgical generator connection to provide a therapeutic drive signal to the energy element.

2. The surgical device of clause 1, wherein the energy storage device comprises at least one capacitor.

3. The surgical device of clause 1, wherein the energy storage device comprises at least one battery.

4. The surgical device of clause 1, further comprising a switch device positioned between the surgical generator connection and the energy storage device and between the surgical generator connection and the at least one energy element, wherein the switch is configured to alternately electrically connect the surgical generator connection to the energy storage device or to the at least one energy element.

5. The surgical device of clause 1, further comprising a signal separator circuit positioned between the surgical generator connection and the energy storage device and between the surgical generator connection at the at least one energy element, wherein the signal separator circuit is configured to receive a combined signal and divide the drive signal into a charge signal portion that is directed to the energy storage device and a therapeutic drive signal portion that is directed towards the at least one energy element.

6. The surgical device of clause 5, wherein the signal separator circuit comprises at least one of a rectifier and a frequency-dependent filter.

7. The surgical device of clause 1, further comprising a memory circuit storing information describing the surgical device, wherein the information comprises an indication that the surgical device is configured to harvest energy from a surgical generator.

8. The surgical device of claim 1, wherein the at least one energy element comprises at least one of the group consisting of: at least one electrodes positioned at the end effector; and an ultrasonic transducer, and wherein the surgical device further comprises an ultrasonic waveguide and an ultrasonic blade in mechanical communication with the transducer.

9. The surgical device of claim 1, wherein the energy storage device is positioned at at least one location selected from the group consisting of: integral to the surgical device; and external to the surgical device.

10. The surgical device of clause 9, wherein the surgical device is programmed to request from the surgical generator an ultrasonic drive signal to drive the transducer and alternately requesting from the surgical generator an charge signal to charge the energy storage device.

11. A method of operating a surgical device in conjunction with a surgical generator, wherein the surgical device comprises an energy storage device in electrical communication with a surgical generator to provide energy to charge the energy storage device and in electrical communication with at least one load component to be powered by the energy storage device; and at least one energy element for treating tissue, the method comprising: receiving a drive signal from the generator; in a first mode, direct at least a portion of the drive signal to the energy storage device; in a second mode, direct at least a portion of the drive signal to at least one energy element.

12. The method of clause 11, wherein the energy storage device comprises at least one capacitor.

13. The method of clause 11, wherein the energy storage device comprises at least one battery.

14. The method of clause 11, wherein the drive signal is a charge signal during a first time period and is a therapeutic drive signal during a second time period, the method further comprising: during the first time period, configuring a switch of the surgical device such that the charge signal is directed to the energy storage device; and during the second time period, configuring the switch of the surgical device such that the therapeutic drive signal is directed to the at least one energy element.

15. The method of clause 11, wherein the drive signal comprises a simultaneously provided charge signal portion and therapeutic drive signal portion, the method further comprising: separating the charge signal portion from the therapeutic drive signal portion; providing the charge signal portion to the energy storage device; and providing the therapeutic drive signal portion to the at least one energy element.

16. The method of clause 15, wherein the separating is performed by at least one components selected from the group consisting of a rectifier and a frequency-dependent filter.

17. The method of clause 11, the method further comprising providing to the surgical generator at least one characteristic of the surgical device, wherein the at least one surgical characteristic indicates that the surgical device is configured to harvest energy from the surgical generator.

18. The method of claim 11, wherein the at least one energy element comprises at least one of the group consisting of: at least one electrode positioned at the end effector; and an ultrasonic transducer, and wherein the surgical device further comprises an ultrasonic waveguide and an ultrasonic blade in mechanical communication with the transducer.

19. The method of claim 11, wherein the energy storage device is positioned at at least one location selected from the group consisting of: integral to the surgical device; and external to the surgical device.

20. The method of clause 19, further comprising: requesting from the surgical generator an ultrasonic drive signal to drive the transducer; and alternately requesting from the surgical generator an charge signal to charge the energy storage device.

We claim:

1. A surgical device for use with a surgical generator, the surgical device comprising:
    an energy storage device, the energy storage device in electrical communication with a surgical generator connection to provide energy from a surgical generator to charge the energy storage device and in electrical communication with at least one load component to be powered by the energy storage device;
    an end effector;
    at least one energy element for treating tissue, wherein the at least one energy element is in electrical communication with the surgical generator connection to provide a therapeutic drive signal to the at least one energy element; and
    a signal separator circuit positioned between the surgical generator connection and the energy storage device and between the surgical generator connection and the at least one energy element, wherein the signal separator circuit is configured to receive a combined signal and divide the combined signal into a charge signal portion that is directed to the energy storage device and a therapeutic drive signal portion that is directed towards the at least one energy element, wherein the therapeutic drive signal portion is configured to provide electrical energy to the tissue sufficient for treating the tissue, wherein the surgical device is configured to direct the charge signal portion to the energy storage device and the therapeutic drive signal portion to the at least one energy element simultaneously,
    wherein the charge signal portion and the therapeutic drive signal portion are present in the combined signal at different frequencies or phases.

2. The surgical device of claim 1, wherein the energy storage device comprises at least one capacitor.

3. The surgical device of claim 1, wherein the energy storage device comprises at least one battery.

4. The surgical device of claim 1, wherein the signal separator circuit comprises at least one of a rectifier and a frequency-dependent filter.

5. The surgical device of claim 1, further comprising a memory circuit storing information describing the surgical device, wherein the information comprises an indication that the surgical device is configured to harvest energy from a surgical generator.

6. The surgical device of claim 1, wherein the at least one energy element comprises at least one of the group consisting of: at least one electrode positioned at the end effector; and an ultrasonic transducer.

7. The surgical device of claim 1, wherein the energy storage device is positioned in at least one location selected from the group consisting of: integral to the surgical device; and external to the surgical device.

8. The surgical device of claim 7, wherein the surgical device is programmed to request, from the surgical generator, an ultrasonic drive signal to drive an ultrasonic transducer and, alternately, requesting, from the surgical generator, a charge signal to charge the energy storage device.

9. The surgical device of claim 1, further comprising a charge management circuit configured to monitor a level of charge on the energy storage device.

10. The surgical device of claim 6, wherein the surgical device further comprises an ultrasonic waveguide and an ultrasonic blade in mechanical communication with the ultrasonic transducer.

11. A surgical system comprising:
    a surgical generator; and
    a surgical device comprising:
        an energy storage device, the energy storage device in electrical communication with a surgical generator connection to provide energy from the surgical generator to charge the energy storage device and in electrical communication with at least one load component to be powered by the energy storage device;
        an end effector;
        at least one energy element for treating tissue, wherein the at least one energy element is in electrical communication with the surgical generator connection to provide a therapeutic drive signal to the at least one energy element; and
        a signal separator circuit positioned between the surgical generator connection and the energy storage device and between the surgical generator connection and the at least one energy element, wherein the signal separator circuit is configured to receive a combined signal and divide the combined signal into a charge signal portion that is directed to the energy storage device and a therapeutic drive signal portion that is directed towards the at least one energy element, wherein the therapeutic drive signal portion is configured to provide electrical energy to the tissue sufficient for treating the tissue, wherein the surgical device is configured to direct the charge signal portion to the energy storage device and the therapeutic drive signal portion to the at least one energy element simultaneously, wherein the charge signal portion and the therapeutic drive signal portion are present in the combined signal at different frequencies or phases,
    wherein the surgical generator is configured to modify the combined signal to remove either the therapeutic drive signal portion or the charge signal portion from the combined signal.

12. The surgical system of claim 11, wherein the signal separator circuit comprises at least one of a rectifier and a frequency-dependent filter.

13. The surgical system of claim 11, wherein the at least one energy element comprises at least one of the group consisting of: at least one electrode positioned at the end effector; and an ultrasonic transducer.

* * * * *